United States Patent [19]

Douglas et al.

[11] 4,387,225

[45] * Jun. 7, 1983

[54] HETEROCYCLIC ALKYLENE TRIAZINONES

[75] Inventors: George H. Douglas, Malvern; William L. Studt, Harleysville; Chong M. Won, Warrington; Stuart A. Dodson, Lansdale; Jerome J. Zalipsky, Melrose Park, all of Pa.

[73] Assignee: William H. Rorer, Inc., Fort Washington, Pa.

[*] Notice: The portion of the term of this patent subsequent to Jul. 6, 1999, has been disclaimed.

[21] Appl. No.: 262,809

[22] Filed: May 12, 1981

Related U.S. Application Data

[60] Continuation-in-part of Ser. No. 225,198, Jan. 15, 1981, Pat. No. 4,338,441, which is a division of Ser. No. 959,611, Nov. 13, 1978, Pat. No. 4,246,409.

[51] Int. Cl.$^3$ ............... C07D 401/06; C07D 401/14; C07D 417/14; C07D 413/14
[52] U.S. Cl. .................................. 544/212; 544/211; 544/113; 544/83; 544/58.7; 260/243.3; 544/58.6
[58] Field of Search ............... 544/113, 83, 58.7, 211, 544/212, 58.6; 260/243.3

[56] References Cited

U.S. PATENT DOCUMENTS 3,931,102 1/1976 Grossmann et al. ............... 544/211
4,198,409 4/1980 Yelnosky et al. .................. 544/212
4,246,409 1/1981 Douglas et al. .................... 544/211

Primary Examiner—John M. Ford
Attorney, Agent, or Firm—James A. Nicholson; Alexis Barron; Martin F. Savitzky

[57] ABSTRACT

Heterocyclic alkyl s-triazine compounds are prepared from the corresponding amidinourea and amidinothiourea compounds by reacting with an activated form of an acid amide to give respectively substituted s-triazinones and thiones of the formula

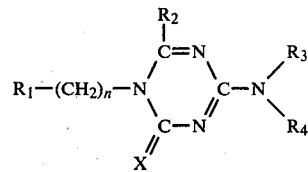

which have pharmacological properties that render them suitable for use for a variety of medicinal purposes, including use as antidiarrheal agents, and which are also useful derivatives in analyzing for the corresponding amidinourea or amidinothiourea precursors.

23 Claims, No Drawings

HETEROCYCLIC ALKYLENE TRIAZINONES

CROSS REFERENCE TO RELATED APPLICATIONS

This is a continuation-in-part of copending application Ser. No. 225,198, filed Jan. 15, 1981, now U.S. Pat. No. 4,338,441, which is a division of application Ser. No. 959,611, filed Nov. 13, 1978, now U.S. Pat. No. 4,246,409.

FIELD OF THE INVENTION

This invention relates to a method for cyclizing amidinoureas and amidinothioureas and to heterocyclic compounds produced by the method. More specifically, this invention relates to heterocyclic alkylene triazinones and triazinthiones.

BACKGROUND

In the above-mentioned U.S. patent application, Ser. No. 959,611, there is disclosed and claimed compounds of the following formula:

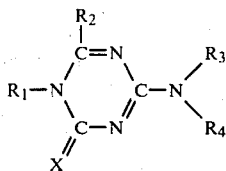

wherein:

X is oxygen or sulfur;

$R_1$ is aryl, aryl lower alkyl, a 5 or 6 membered heterocycle or a lower alkyl substituted 5 or 6 membered heterocycle;

$R_2$ is hydrogen or lower alkyl; and, $R_3$ and $R_4$ are each independently selected from the group consisting of hydrogen, hydroxyl, lower alkanoyl, lower alkyl, cyclo-lower alkyl, lower alkenyl, lower alkynyl, halo-lower alkyl, lower alkoxy-lower alkyl, hydroxy-lower alkyl, phenoxy-lower alkyl, diloweralkyl amino, aryl or aryl-lower alkyl, lower alkoxy, phenoxy, a 5 or 6 membered heterocycle or a lower alkyl substituted 5 or 6 membered heterocycle or $R_3$ and $R_4$ together with the nitrogen to which they are attached form a 3 to 7 membered heterocyclic ring, selected from the group consisting of oxazolidinyl, thiazolidinyl, pyrazolidinyl, imidazolidinyl, piperidyl azepinyl, piperazinyl, thiamorpholinyl, trimethylenetriaminyl, ethyleneiminyl and morpholinyl;

and wherein:

aryl means phenyl or phenyl in which one or more of the phenyl hydrogens has been replaced by the same or different substituents selected from the group consisting of halo, lower alkyl, halo-lower alkyl, nitro, amino, lower alkylacylamino, hydroxy, lower alkoxy, phenyl-lower alkoxy, lower alkyl acyloxy, cyano, halo-lower alkoxy or lower alkyl sulfonyl; and, 5 or 6 membered heterocycle means a heterocyclic substituent selected from the group consisting of pyridyl, pyrimidyl, pyrazolyl, imidazolyl, furyl, thienyl, oxazolyl, thiazolyl, piperidyl, and morpholinyl;

and the non-toxic pharmaceutically acceptable salts thereof. In addition, said application discloses heterocyclic alkylene triazinones, that is, compounds where $R_1$ is a heterocyclic group attached to the triazinone nitrogen atom through an alkylene group.

The present application is directed to, and claims, heterocyclic alkylene triazinones.

SUMMARY OF THE INVENTION

In accordance with the present invention, there is provided a class of compounds comprising 1,4-substituted-1,2-dihydro-1,3,5-triazine-2-ones and thiones of Formula I.

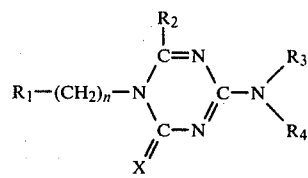

wherein:

n is 1 to 3;

X is oxygen or sulfur;

$R_1$ is a 5 or 6 membered heterocycle or a substituted 5 or 6 membered heterocycle;

$R_2$ is hydrogen or lower alkyl; and $R_3$ and $R_4$ are each independently selected from the group consisting of hydrogen, hydroxyl, lower alkanoyl, lower alkyl, cyclo-lower alkyl, lower alkenyl, lower alkynyl, halo-lower alkyl, lower alkoxy-lower alkyl, hydroxy-lower alkyl, phenoxy-lower alkyl, diloweralkyl amino, aryl or aryl-lower alkyl, lower alkoxy, phenoxy, a 5 or 6 membered heterocycle or a lower alkyl substituted 5 or 6 membered heterocycle or $R_3$ and $R_4$ together with the nitrogen to which they are attached form a 3 to 7 membered heterocyclic ring, selected from the group consisting of oxazolidinyl, thiazolidinyl, pyrazolidinyl, imidazolidinyl, piperidyl azepinyl, piperazinyl, thiamorpholinyl, trimethylenetriaminyl, ethyleneiminyl, and morpholinyl;

and wherein:

aryl means phenyl or phenyl in which one or more of the phenyl hydrogens has been replaced by the same or different substituents selected from the group consisting of halo, lower alkyl, halo-lower alkyl, nitro, amino, lower alkyl acylamino, lower alkyl acyloxy, hydroxy, lower alkoxy, phenyl-lower alkoxy, lower alkanoyl, cyano, halo-lower alkoxy and lower alkyl sulfonyl; and 5 or 6 membered heterocycle means a heterocyclic substituent selected from the group consisting of pyridyl, pyrimidyl, pyrazolyl, imidazolyl, furyl, thienyl, oxazolyl, thiazolyl, piperidyl, and morpholinyl; and the nontoxic pharmaceutically acceptable salts thereof.

DETAILED DESCRIPTION OF THE INVENTION

Depending upon the specific substitution, compounds of Formula I above may be present in enolized or tautomeric forms. Certain of the compounds can also be obtained as hydrates or in different polymorphic forms. The structures used herein to designate novel compounds are intended to include the compound shown along with its alternative or transient states. The nomenclature generally employed to identify the novel triazine derivatives as disclosed herein is based upon the ring structure shown in Formula I with the triazine ring positions numbered counterclockwise beginning with the nitrogen having the $R_1$ substitution.

Heterocyclic alkylene s-triazinones and s-triazinthiones of this invention which form a preferred class of novel compounds are those represented by Formula I, where $R_1$ is pyridyl. The preferred pyridyl group is 2-pyridyl or substituted 3- or 4-pyridyls in which one or both pyridyl ring carbons vicinal to the carbon attached to the triazinone ring are substituted by lower alkyl, lower alkoxy, or halo lower alkyl.

When
$R_1$ is substituted 3- or 4-pyridyl, thienyl or
furyl, the preferred substituents on the heterocyclic ring moiety are lower alkyl, hydroxyl, halo, and lower alkoxy.

A preferred group of novel triazinones are compounds of the formula

I-a wherein:
n is 1 to 3;
$R_2$ is hydrogen or lower alkyl;
$R_5$, $R_6$, $R_7$ and $R_8$ are the same or different and are $C_1$ to $C_4$ alkyl, bromo, chloro, hydroxy, acyloxy, lower alkanoyl, or $C_1$ to $C_4$ alkoxy; and
$R_3$ and $R_4$ are each hydrogen, lower alkyl, hydroxy, lower alkoxy, phenoxy, dilower alkyl amino lower alkyl, lower alkanoyl, lower alkenyl, and lower alkynyl; or
$R_3$ and $R_4$ together with the nitrogen to which they are attached form a 5 or 6 membered heterocyclic ring which may be pyrrolidinyl, oxazolidinyl, thiazolidinyl, pyrazolidinyl, imidazolidinyl, piperidyl, piperazinyl, thiamorpholinyl, or morpholinyl.

A most preferred group of heterocylic alkylene triazinones are compounds of the formula I-b.

I-b wherein:
n is 1 to 3;
$R_3$ is hydrogen, hydroxy, lower alkyl, lower alkoxy, or dilower alkyl amino lower alkyl; and
$R_5$ is lower alkyl, hydrogen, hydroxy, halo, halo lower alkyl, or lower alkoxy.

A special embodiment of this invention comprises pyridyl-N-oxides of 1-(2-pyridyl-alkylene) triazinones.

As employed above and throughout the disclosure, the following terms, unless otherwise indicated, shall be understood to have the following meanings:

"alkyl" means a saturated aliphatic hydrocarbon which may be either straight or branched chain preferably having no more than about 20 carbon atoms; lower alkyl being preferred; also included are the cyclo alkyl groups such as cyclo hexyl, cyclo propyl etc, and the cycloalkyl alkyl groups such as cyclo propylmethyl and the like.

"lower alkyl" means an alkyl group as above, having 1 to 6 carbon atoms, suitable lower alkyl groups are methyl, ethyl, propyl, isopropyl, butyl, sec-butyl, tert-butyl, pentyl and isopentyl.

"cycloalkyl" means an aliphatic monocyclic saturated carbocyclic group having 3 to 6 carbon atoms preferably cyclopropyl, cyclopentyl, and cyclohexyl.

"alkenyl" means an unsaturated aliphatic hydrocarbon having no more than about 20 carbon atoms and which contains one or more double bonds and which may be straight or branched chain with lower alkenyl, i.e. alkenyl of 2 to 6 carbons, being preferred.

"lower alkenyl" means alkenyl of 2 to 6 carbon atoms such as ethylene, propylene, butylene, isobutylene, etc.

"alkynyl" means an unsaturated aliphatic hydrocarbon having no more than about 20 carbon atoms and containing one or more triple bonds with lower alkynyl, i.e. alkynyl of 2 to 6 carbon atoms such as propargyl, butynyl, pentynyl, etc.

"aryl" means phenyl and substituted phenyl.

"substituted phenyl" means a phenyl group in which one or more of the phenyl hydrogens has been replaced by the same or different substituents including halo, lower alkyl, halo lower alkyl, nitro, amino, acylamino, hydroxy, lower alkoxy, aryl-lower alkoxy, acyloxy, cyano, halolower alkoxy, or lower alkyl sulfonyl.

"aralkyl" means an alkyl (preferably a lower alkyl) in which one or more hydrogens is substituted by an aryl moiety (preferably phenyl or substituted phenyl), e.g. benzyl, phenethyl, etc. "5 and 6 membered heterocyclic group" means a 5 or 6 membered ring having 1 to 3 hetero atoms which may be nitrogen, oxygen or sulfur including pyridyl, (2-pyridyl, 3-pyridyl or 4-pyridyl), pyrazolyl, imidazolyl, furyl, thienyl, oxazolyl, thiazolyl, piperidyl, morpholinyl.

"substituted 5 to 6 membered heterocycle" means a heterocycle in which one or more of the hydrogens on the ring carbons have been replaced by substituents as given above with respect to substituted phenyl.

The terms "halo" and "halogen" include all four halogens, namely, fluorine, chlorine, bromine and iodine. The halo alkyls, halophenyl and halosubstituted pyridyl include groups having more than one halo substituent which may be the same or different such as trifluoromethyl, 1-chloro-2-bromo ethyl, chlorophenyl, 4-chloropyridyl, etc.

The term "acyloxy" is intended to mean an organic acid radical such as acetoxy, propionoxy, and the like.

The term "lower alkanoyl" is intended to include the acid radical of a lower alkanoic acid such as acetyl, propionyl, and the like.

The novel compounds of this invention may be synthesized according to the novel cyclizing reaction as illustrated schematically below:

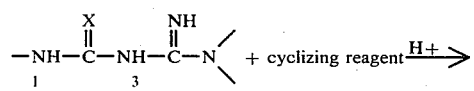

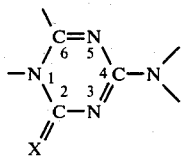

wherein X is sulfur or oxygen indicating that the reaction can employ as starting material either an amidinourea or amidinothiourea. The dangling bonds may be substituted by any appropriate substituent determined by available amidinourea or amidinothiourea starting material. The dangling bonds on the end product 1,3,5-triazin-2-one or 1,3,5-triazine-2-thione, will be substituted by groups corresponding to similar substituents on the starting materials.

It has been found that an amidinourea can be cyclized to the corresponding s-triazinone by condensing the amidinourea with an organic reagent having an activated methylidene group or capable of forming an activated methylidene, for example, a methylidene group having at least one available hydrogen atom and a leaving group such as a di-substituted amino group attached to the methylidene carbon. The organic reagent used for condensing the amidinourea starting material to form the corresponding s-triazinone may be an activated form of an acid amide, an ortho ester or acyl derivative, such as, a Vilsmeir reagent which will bring about acylation and ring closure of the amidinourea or thiourea to give s-triazinones of Formula I above. The cyclizing process can be used in the same manner to prepare s-triazinthiones from the corresponding amidinothioureas and it will be understood that in referring to the preparation of triazinones it is intended to include also the thiones. The reagent may be the dialkylacetal of a di-alkyl-lower carboxylic acid amide or the reaction product of a di-alkyllower carboxylic acid amide and an alkylating agent. The reagent can be prepared in situ or in advance depending upon its stability. The synthesis of triazinones according to this invention can employ as starting material known amidinoureas or similar starting materials also known in the art, or the materials employed as precursors for cyclizing to form s-triazinones can be readily prepared by analogy to the preparation of the known starting materials. Suitable amidinourea starting materials are those disclosed in copending U.S. patent application Ser. No. 262,808, U.S. Pat. Nos. 4,060,635; 4,058,557; and 4,178,387, the disclosures of which are incorporated herein by reference. Thus, the novel cyclizing process of this invention can be used to derivatize amidinoureas and thioureas of Formula II below.

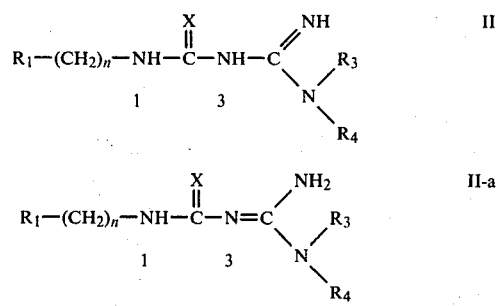

wherein n is 1 to 3 and X, $R_1$, $R_3$ and $R_4$ have the same meanings as above.

It should be understood that whereas the structure of the starting materials are shown here in a particular configuration for the purposes of illustration, it is intended to include the various structural isomers as previously noted. By way of illustration, an alternative structure is shown by Formula II-a. Where reference is made to the terminal nitrogens, it is intended to denote the urea nitrogen designated as position 1 in Formula II and the unsubstituted amidino nitrogen.

The 1,3,5-triazin-2-ones and 1,3,5-triazin-2-thiones may be prepared according to this invention utilizing as starting materials any of the prior art amidinoureas or amidinothioureas including the 1-pyridylalkylene amidinoureas and thioureas of Formula IV below which constitute a preferred group of starting materials.

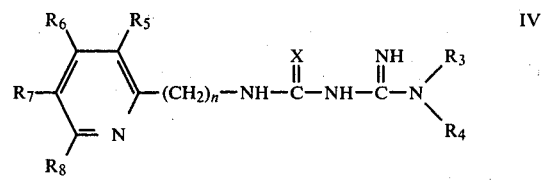

wherein:

n is 1 to 3; and X and the $R_3$ through $R_8$ substituents have the same meanings as the corresponding substituents on the novel triazines of Formula I-a described hereinabove.

Amidinourea starting materials which can be used to prepare a preferred group of triazine derivatives are those wherein:

$R_3$ and $R_4$ are hydrogen,
hydroxy,
lower alkyl,
lower alkoxy,
halo lower alkyl, or
aralkyl, or
$R_3$ and $R_4$ together may form with the nitrogen to which they are attached a 5 to 7 atom ring which may include 0 to 2 hetero atoms of N, O or S.

An even more preferred group of starting materials include those where:

R$_5$, R$_6$, R$_7$ and R$_8$ are hydrogen,
halo,
lower alkyl,
halo lower alkyl,
nitro,
hydroxy or
lower alkoxy.

A special embodiment of this invention comprises compounds prepared from starting materials according to Formula IV wherein:
n is 1 or 2;
X is oxygen;
R$_5$ and R$_8$ are the same or different and are hydrogen, lower alkyl, lower alkoxy, or halo;
and one of R$_3$ and R$_4$ is hydrogen and the other is
lower alkyl,
halo lower alkyl,
hydroxy,
lower alkoxy or
acyl.

Using the general method for cyclizing amidinoureas described above, and employing, by way of illustration, as the starting material any of the amidinoureas in Tables I and I-a below, there can be obtained the corresponding triazinones. Tables II, II-a and V set forth examples of triazinones within the scope of the present invention.

The thione analogs and their salts are prepared in the same manner using the corresponding amidinothiourea as starting material. Examples of amidinothiourea starting materials are given in Table III. Examples of triazine thiones within the scope of the present invention are set forth in Tables IV and V.

TABLE I 1-(2'-pyridylmethyl)-3-methylamidinourea
1-(2'-pyridylmethyl)-3-ethylamidinourea
1-(2'-pyridylmethyl)-3-propylamidinourea
1-(2'-pyridylmethyl)-3-i-propylamidinourea
1-(2'-pyridylmethyl)-3-butylamidinourea
1-(2'-pyridylmethyl)-3-i-butylamidinourea
1-(2'-pyridylmethyl)-3-pentylamidinourea
1-(2'-pyridylmethyl)-3-propargylamidinourea
1-(2'-pyridylmethyl)-3-allylamidinourea
1-(2'-pyridylmethyl)-3-methoxyethylamidinourea
1-(2'-pyridylmethyl)-3-benzyloxyethylamidinourea
1-(2'-pyridylmethyl)-3-phenethoxyethylamidinourea
1-(2'-pyridylmethyl)-3-(N,N—dimethylamidino)urea
1-(2'-pyridylmethyl)-3-(N,N—diethylamidino)urea
1-(2'-pyridylmethyl)-3-(N,N—tetramethyleneamidino)urea
1-(2'-pyridylmethyl)-3-(N,N—pentamethyleneamidino)urea
1-(2'-pyridylmethyl)-3-(N,N—hexamethyleneamidino)urea
1-(3'-methyl-2'-pyridylmethyl)-3-methylamidinourea
1-(3'-methyl-2'-pyridylmethyl)-3-ethylamidinourea
1-(3'-methyl-2'-pyridylmethyl)-3-propylamidinourea
1-(3'-methyl-2'-pyridylmethyl)-3-i-propylamidinourea
1-(3'-methyl-2'-pyridylmethyl)-3-i-butylamidinourea
1-(3'-methyl-2'-pyridylmethyl)-3-pentylamidinourea
1-(3'-methyl-2'-pyridylmethyl)-3-allylamidinourea
1-(3'-methyl-2'-pyridylmethyl)-3-propargylamidinourea
1-(3'-methyl-2'-pyridylmethyl)-3-cyclopropylamidinourea
1-(3'-methyl-2'-pyridylmethyl)-3-methoxyethylamidinourea
1-(3'-methyl-2'-pyridylmethyl)-3-benzyloxyethylamidinourea
1-(3'-methyl-2'-pyridylmethyl)-3-phenethoxyethylamidinourea
1-(3'-methyl-2'-pyridylmethyl)-3-benzylamidinourea
1-(3'-methyl-2'-pyridylmethyl)-3-(N,N—dimethylamidino)urea
1-(3'-methyl-2'-pyridylmethyl)-3-(N,N—diethylamidino)urea
1-(3'-methyl-2'-pyridylmethyl)-3-(N,N—tetramethyleneamidino)urea
1-(3'-methyl-2'-pyridylmethyl)-3-(N,N—pentamethyleneamidino)urea
1-(3'-chloro-2'-pyridylmethyl)-3-methylamidinourea
1-(3'-chloro-2'-pyridylmethyl)-3-ethylamidinourea
1-(3'-chloro-2'-pyridylmethyl)-3-propylamidinourea
1-(3'-chloro-2'-pyridylmethyl)-3-i-propylamidinourea TABLE I-continued 1-(3'-chloro-2'-pyridylmethyl)-3-butylamidinourea
1-(3'-chloro-2'-pyridylmethyl)-3-i-butylamidinourea
1-(3'-chloro-2'-pyridylmethyl)-3-t-butylamidinourea
1-(3'-chloro-2'-pyridylmethyl)-3-pentylamidinourea
1-(3'-chloro-2'-pyridylmethyl)-3-allylamidinourea
1-(3'-chloro-2'-pyridylmethyl)-3-propargylamidinourea
1-(3'-chloro-2'-pyridylmethyl)-3-cyclopropylamidinourea
1-(3'-chloro-2'-pyridylmethyl)-3-cyclobutylamidinourea
1-(3'-chloro-2'-pyridylmethyl)-3-(N—[3'-cyclopentenyl]amidino)urea
1-(3'-chloro-2'-pyridylmethyl)-3-cyclopropylmethylamidinourea
1-(3'-chloro-2'-pyridylmethyl)-3-methoxyethylamidinourea
1-(3'-chloro-2'-pyridylmethyl)-3-benzyloxyethylamidinourea
1-(3'-chloro-2'-pyridylmethyl)-3-phenethoxyethylamidinourea
1-(3'-chloro-2'-pyridylmethyl)-3-benzylamidinourea
1-(3'-chloro-2'-pyridylmethyl)-3-(N,N—dimethylamidino)urea
1-(3'-chloro-2'-pyridylmethyl)-3-(N,N—diethylamidino)urea
1-(3'-chloro-2'-pyridylmethyl)-3-(N,N—tetramethyleneamidino)urea
1-(2'-pyridylmethyl)-3-(N,N[3'-methyl-3'-azapentamethylene]-amidino)urea
1-(2'-pyridylmethyl)-3-(N,N[3'-oxapentamethylene]amidino)urea
1-(3'-pyridylmethyl)-3-methylamidinourea
1-(3'-pyridylmethyl)-3-ethylamidinourea
1-(3'-pyridylmethyl)-3-propylamidinourea
1-(3'-pyridylmethyl)-3-i-propylamidinourea
1-(3'-pyridylmethyl)-3-butylamidinourea
1-(3'-pyridylmethyl)-3-i-butylamidinourea
1-(3'-pyridylmethyl)-3-t-butylamidinourea
1-(3'-pyridylmethyl)-3-pentylamidinourea
1-(3'-pyridylmethyl)-3-allylamidinourea
1-(3'-pyridylmethyl)-3-propargylamidinourea
1-(3'-pyridylmethyl)-3-cyclobutylamidinourea
1-(3'-pyridylmethyl)-3-cyclohexylamidinourea
1-(3'-pyridylmethyl)-3-benzylamidinourea
1-(3'-pyridylmethyl)-3-methoxyethylamidinourea
1-(3'-pyridylmethyl)-3-benzyloxyethylamidinourea
1-(3'-pyridylmethyl)-3-methoxyethylamidinourea
1-(3'-pyridylmethyl)-3-benzyloxyethylamidinourea
1-(3'-pyridylmethyl)-3-phenethoxyethylamidinourea
1-(3'-pyridylmethyl)-3-(N,N—dimethylamidino)urea
1-(3'-pyridylmethyl)-3-(N,N—diethylamidino)urea
1-(3'-pyridylmethyl)-3-(N,N—pentamethyleneamidino)urea
1-(4'-pyridylmethyl)-3-methylamidinourea
1-(4'-pyridylmethyl)-3-ethylamidinourea
1-(4'-pyridylmethyl)-3-propylamidinourea
1-(4'-pyridylmethyl)-3-i-propylamidinourea
1-(4'-pyridylmethyl)-3-butylamidinourea
1-(4'-pyridylmethyl)-3-t-butylamidinourea
1-(4'-pyridylmethyl)-3-pentylamidinourea
1-(4'-pyridylmethyl)-3-hexylamidinourea
1-(4'-pyridylmethyl)-3-propargylamidinourea
1-(4'-pyridylmethyl)-3-allylamidinourea
1-(4'-pyridylmethyl)-3-methoxyethylamidinourea
1-(4'-pyridylmethyl)-3-benzyloxyethylamidinourea
1-(4'-pyridylmethyl)-3-phenethoxyethylamidinourea
1-(4'-pyridylmethyl)-3-(N,N—dimethylamidino)urea
1-(4'-pyridylmethyl)-3-(N,N—diethylamidino)urea
1-(4'-pyridylmethyl)-3-(N—methyl-N—ethylamidino)urea
1-(4'-pyridylmethyl)-3-(N,N—tetramethyleneamidino)urea
1-(4'-pyridylmethyl)-3-(N,N—pentamethyleneamidino)urea
1-(4'-pyridylmethyl)-3-(N,N—hexamethyleneamidino)urea
1-(2'-ethyl-4'-pyridylmethyl)-3-methylamidinourea
1-(2'-ethyl-4'-pyridylmethyl)-3-ethylamidinourea
1-(2'-ethyl-4'-pyridylmethyl)-3-propylamidinourea
1-(2'-ethyl-4'-pyridylmethyl)-3-butylamidinourea
1-(2'-ethyl-4'-pyridylmethyl)-3-i-butylamidinourea
1-(2'-ethyl-4'-pyridylmethyl)-3-pentylamidinourea
1-(2'-ethyl-4'-pyridylmethyl)-3-allylamidinourea
1-(2'-ethyl-4'-pyridylmethyl)-3-propargylamidinourea
1-(2'-ethyl-4'-pyridylmethyl)-3-methoxyethylamidinourea
1-(2'-ethyl-4'-pyridylmethyl)-3-benzyloxyethylamidinourea
1-(2'-ethyl-4'-pyridylmethyl)-3-(N,N—dimethylamidino)urea
1-(2'-ethyl-4'-pyridylmethyl)-3-(N,N—diethylamidino)urea
1-(2'-ethyl-4'-pyridylmethyl)-3-(N,N—tetramethyleneamidino)urea
1-(2',6'-dichloro-4'-pyridylmethyl)-3-methylamidinourea
1-(2',6'-dimethyl-4'-pyridylmethyl)-3-methylamidinourea
1-(2'-methyl,6'-chloro-4'-pyridylmethyl)-3-methylamidinourea
1-(2'-thiophenylmethyl)-3-methylamidinourea
1-(3'-thiophenylmethyl)-3-methylamidinourea
1-(5'-methyl-2'-thiophenylmethyl)-3-methylamidinourea
1-(5'-chloro-2'-thiophenylmethyl)-3-methylamidinourea
1-(2'-pyridlmethyl-N—oxide)-3-(N,N—dimethylamidino)urea
1-(3'-cyano-2'-pyridylmethyl)-3-(N—methylamidino)urea

TABLE I-continued 1-(3'-carbomethoxy-2'-pyridylmethyl)-3-(N—methylamidino)urea
1-(3'-carboethoxy-2'-pyridylmethyl)-3-(N—methylamidino)urea
1-(6'-chloro-2'-pyridylmethyl)-3-(N—methylamidino)urea
1-(6'-methyl-2'-pyridylmethyl)-3-(N—methylamidino)urea
1-(3'-ethyl-2'-pyridylmethyl)-3-(N—methylamidino)urea
1-(2'-methyl-3'-pyridylmethyl)-3-(N—methylamidino)urea
1-(2'-ethyl-3'-pyridylmethyl)-3-(N—methylamidino)urea
1-(2',6'-dimethyl-3'-pyridylmethyl)-3-(N—methylamidino)urea
1-(3'-cyano-2'-thiophenylmethyl)-3-(N—methylamidino)urea
1-(3'-carbomethoxy-2'-thiophenylmethyl)-3-(N—methylamidino)urea
1-(3'-carboethoxy-2'-thiophenylmethyl)-3-(N—methylamidino)urea
1-(2'-methoxy-3'-pyridylmethyl)-3-(N—methylamidino)urea
1-(2'-ethoxy-3'-pyridylmethyl)-3-(N—methylamidino)urea
1-(2'-chloro-3'-pyridylmethyl)-3-(methylamidino)urea
1-furfuryl-3-amidinourea
1-(3'-methyl-furfuryl)-3-amidinourea
1-furfuryl-3-(N—ethylamidino)urea
1-furfuryl-3-(N—propylamidino)urea
1-furfuryl-3-(N— i-propylamidino)urea
1-furfuryl-3-(N—butylamidino)urea
1-furfuryl-3-(N—i-butylamidino)urea
1-furfuryl-3-(N—sec-butylamidino)urea
1-furfuryl-3-(N—t-butylamidino)urea
1-furfuryl-3-(N—pentylamidino)urea
1-furfuryl-3-(N—hexylamidino)urea
1-furfuryl-3-(N—heptylamidino)urea
1-furfuryl-3-(N—cyclopropylamidino)urea
1-furfuryl-3-(N—cyclobutylamidino)urea
1-(2'-pyridylmethyl-N—oxide)-3-methylamidinourea
1-(3'-pyridylmethyl-N—oxide)-3-methylamidinourea
1-(4'-pyridylmethyl-N—oxide)-3-methylamidinourea
1-furfuryl-3-methylamidinourea
1-tetrahydrofurfuryl-3-methylamidinourea
1-(1'-imidazolylmethyl)-3-methylamidinourea
1-(2'-imidazolylmethyl)-3-methylamidinourea
1-(4'-imidazolylmethyl)-3-methylamidinourea
1-(2'-oxazolylmethyl)-3-methylamidinourea
1-(4'-oxazolylmethyl)-3-methylamidinourea
1-(5'-oxazolylmethyl)-3-methylamidinourea
1-(2'-thiazolylmethyl)-3-methylamidinourea
1-(4'-thiazolylmethyl)-3-methylamidinourea
1-(5'-thiazolylmethyl)-3-methylamidinourea
1-(1'-pyrazolylmethyl)-3-methylamidinourea
1-(1'-[3'-pyrrolidinyl]methyl)-3-methylamidinourea
1-(2'-pyrrolidinylmethyl)-3-methylamidinourea
1-(4'-morpholinylmethyl)-3-methylamidinourea
1-(2'-morpholinylmethyl)-3-methylamidinourea
1-(2'-pyrimidinylmethyl)-3-methylamidinourea
1-(4'-pyrimidinylmethyl)-3-methylamidinourea
1-(2'-quinolylmethyl)-3-methylamidinourea
1-(4'-quinolylmethyl)-3-methylamidinourea
1-(1'-isoquinolylmethyl)-3-methylamidinourea
1-furfuryl-3-(N—cyclopentylamidino)urea
1-furfuryl-3-(N—cyclohexylamidino)urea
1-furfuryl-3-(N—phenylamidino)urea
1-furfuryl-3-(N—benzylamidino)urea
1-furfuryl-3-(N—phenethylamidino)urea
1-furfuryl-3-(N—methyl-N—benzylamidino)urea
1-furfuryl-3-(N,N—dibenzylamidino)urea
1-tetrahydrofurfuryl-3-amidinourea
1-(3'-methyl-tetrahydrofurfuryl)-3-amidinourea
1-(2'-methyl-tetrahydrofurfuryl)-3-amidinourea
1-(1'-imidazolylmethyl)-3-amidinourea
1-(2'-methyl-1'-imidazolylmethyl)-3-amidinourea
1-(4'-imidazolylmethyl)-3-amidinourea
1-(1'-methyl-4'-imidazolylmethyl)-3-amidinourea
1-(2'-methyl-4'-imidazolylmethyl)-3-amidinourea
1-(2'-imidazolylmethyl)-3-amidinourea
1-(2'-oxazolylmethyl)-3-amidinourea
1-(4'-methyl-2'-oxazolylmethyl)-3-amidinourea
1-(4'-oxazolylmethyl)-3-amidinourea
1-(4'-methyl-2'-oxazolylmethyl)-3-amidinourea
1-(4'-oxazolylmethyl)-3-amidinourea
1-(5'-oxazolylmethyl)-3-amidinourea
1-(2'-methyl-5'-oxazolylmethyl)-3-amidinourea
1-(4'-thiazolylmethyl)-3-amidinourea
1-(5'-methyl-4'-thiazolylmethyl)-3-amidinourea
1-(5'-thiazolylmethyl)-3-amidinourea
1-(4'-methyl-5'-thiazolylmethyl)-3-amidinourea
1-(1'-pyrazolylmethyl)-3-amidinourea
1-(3'-pyrrolylmethyl)-3-amidinourea
1-(2'-methyl-3'-pyrrolylmethyl)-3-amidinourea
1-(3'-methyl-2'-pyrrolylmethyl)-3-amidinourea
1-(1'-pyrrolidinylmethyl)-3-amidinourea
1-(2'-methyl-1'-pyrrolidinylmethyl)-3-amidinourea
1-(1'-pyrrolidinylmethyl)-3-amidinourea
1-(4'-morpholinylmethyl)-3-amidinourea
1-(2'-methyl-4'-morpholinylmethyl)-3-amidinourea
1-(2'-morpholinylmethyl)-3-amidinourea
1-(4'-methyl-2'-morpholinylmethyl)-3-amidinourea
1-(2'-methyl-2'-morpholinylmethyl)-3-amidinourea
1-(3'-morpholinylmethyl)-3-amidinourea
1-(4'-methyl-3'-morpholinylmethyl)-3-amidinourea
1-(2'-methyl-3'-morpholinylmethyl)-3-amidinourea
1-(2'-pyrimidinylmethyl)-3-amidinourea
1-(4'-methyl-2'-pyrimidinylmethyl)-3-amidinourea
1-(4'-pyrimidinylmethyl)-3-amidinourea
1-(2'-methyl-4'-pyrimidinylmethyl)-3-amidinourea
1-(2'-quinolylmethyl)-3-amidinourea
1-(3'-methyl-2'-quinolylmethyl)-3-amidinourea
1-(4'-quinolylmethyl)-3-amidinourea
1-(3'-methyl-4'-quinolylmethyl)-3-amidinourea
1-(1'-isoquinolylmethyl)-3-amidinourea
1-[2-(2'-pyridyl)ethyl]-3-methylamidinourea
1-[2-(2'-pyridyl)ethyl]-3-ethylamidinourea
1-[2-(2'-pyridyl)ethyl]-3-propylamidinourea
1-[2-(2'-pyridyl)ethyl]-3-i-propylamidinourea
1-[2-(2'-pyridyl)ethyl]-3-butylamidinourea
1-[2-(2'-pyridyl)ethyl]-3-i-butylamidinourea
1-[2-(2'-pyridyl)ethyl]-3-pentylamidinourea
1-[2-(2'-pyridyl)ethyl]-3-propargylamidinourea
1-[2-(2'-pyridyl)ethyl]-3-allylamidinourea
1-[2-(2'-pyridyl)ethyl]-3-methoxyethylamidinourea
1-[2-(2'-pyridyl)ethyl]-3-benzyloxyethylamidinourea
1-[2-(2'-pyridyl)ethyl]-3-phenethoxyethylamidinourea
1-[2-(2'-pyridyl)ethyl]-3-(N,N—dimethylamidino)urea
1-[2-(2'-pyridyl)ethyl]-3-(N,N—diethylamidino)urea
1-[2-(2'-pyridyl)ethyl]-3-(N,N—tetramethyleneamidino)urea
1-[2-(2'-pyridyl)ethyl]-3-(N,N—pentamethyleneamidino)urea
1-[2-(2'-pyridyl)ethyl]-3-(N,N—hexamethyleneamidino)urea
1-[2-(3'-methyl-2'-pyridyl)ethyl]-3-methylamidinourea
1-[2-(3'-methyl-2'-pyridyl)ethyl]-3-ethylamidinourea
1-[2-(3'-methyl-2'-pyridyl)ethyl]-3-propylamidinourea
1-[2-(3'-methyl-2'-pyridyl)ethyl]-3-i-propylamidinourea
1-[2-(3'-methyl-2'-pyridyl)ethyl]-3-i-butylamidinourea
1-[2-(3'-methyl-2'-pyridyl)ethyl]-3-pentylamidinourea
1-[2-(3'-methyl-2'-pyridyl)ethyl]-3-allylamidinourea
1-[2-(3'-methyl-2'-pyridyl)ethyl]-3-propargylamidinourea
1-[2-(3'-methyl-2'-pyridyl)ethyl]-3-cyclopropylamidinourea
1-[2-(3'-methyl-2'-pyridyl)ethyl]-3-methoxyethylamidinourea
1-[2-(3'-methyl-2'-pyridyl)ethyl]-3-benzyloxyethylamidinourea
1-[2-(3'-methyl-2'-pyridyl)ethyl]-3-phenethoxyethylamidinourea
1-[2-(3'-methyl-2'-pyridyl)ethyl]-3-benzylamidinourea
1-[2-(3'-methyl-2'-pyridyl)ethyl]-3-(N,N—dimethylamidino)urea
1-[2-(3'-methyl-2'-pyridyl)ethyl]-3-(N,N—diethylamidino)urea
1-[2-(3'-methyl-2'-pyridyl)ethyl]-3-(N,N—tetramethyleneamidino)urea
1-[2-(3'-methyl-2'-pyridyl)ethyl]-3-(N,N—pentamethyleneamidino)urea
1-[2-(3'-chloro-2'-pyridyl)ethyl]-3-methylamidinourea
1-[2-(3'-chloro-2'-pyridyl)ethyl]-3-ethylamidinourea
1-[2-(3'-chloro-2'-pyridyl)ethyl]-3-propylamidinourea
1-[2-(3'-chloro-2'-pyridyl)ethyl]-3-i-propylamidinourea
1-[2-(3'-chloro-2'-pyridyl)ethyl]-3-butylamidinourea
1-[2-(3'-chloro-2'-pyridyl)ethyl]-3-i-butylamidinourea
1-[2-(3'-chloro-2'-pyridyl)ethyl]-3-t-butylamidinourea
1-[2-(3'-chloro-2'-pyridyl)ethyl]-3-pentylamidinourea
1-[2-(3'-chloro-2'-pyridyl)ethyl]-3-allylamidinourea
1-[2-(3'-chloro-2'-pyridyl)ethyl]-3-propargylamidinourea
1-[2-(3'-chloro-2'-pyridyl)ethyl]-3-cyclopropylamidinourea
1-[2-(3'-chloro-2'-pyridyl)ethyl]-3-cyclobutylamidinourea
1-[2-(3'-chloro-2'-pyridyl)ethyl]-3-(N—[3'-cyclopentenyl]amidino)urea
1-[2-(3'-chloro-2'-pyridyl)ethyl]-3-cyclopropylmethylamidinourea
1-[2-(3'-chloro-2'-pyridyl)ethyl]-3-methoxyethylamidinourea
1-[2-(3'-chloro-2'-pyridyl)ethyl]-3-benzyloxyethylamidinourea
1-[2-(3'-chloro-2'-pyridyl)ethyl]-3-phenethoxyethylamidinourea
1-[2-(3'-chloro-2'-pyridyl)ethyl]-3-benzylamidinourea
1-[2-(3'-chloro-2'-pyridyl)ethyl]-3-(N,N—dimethylamidino)urea
1-[2-(3'-chloro-2'-pyridyl)ethyl]-3-(N,N—diethylamidino)urea
1-[2-(3'-chloro-2'-pyridyl)ethyl]-3-(N,N—tetramethyleneamidino)urea
1-[2-(2'-pyridyl)ethyl]-3-(N,N[3'-methyl-3'-azapentamethylene]-amidino)urea
1-[2-(2'-pyridyl)ethyl]-3-(N,N[3'-oxapentamethylene]amidino)urea
1-[2-(2'-pyridyl)ethyl]-3-methylamidinourea
1-[2-(2'-pyridyl)ethyl]-3-ethylamidinourea

TABLE I-continued

1-[2-(2'-pyridyl)ethyl]-3-propylamidinourea
1-[2-(2'-pyridyl)ethyl]-3-i-propylamidinourea
1-[2-(2'-pyridyl)ethyl]-3-butylamidinourea
1-[2-(2'-pyridyl)ethyl]-3-i-butylamidinourea
1-[2-(2'-pyridyl)ethyl]-3-t-butylamidinourea
1-[2-(3'-pyridyl)ethyl]-3-pentylamidinourea
1-[2-(3'-pyridyl)ethyl]-3-allylamidinourea
1-[2-(3'-pyridyl)ethyl]-3-propargylamidinourea
1-[2-(3'-pyridyl)ethyl]-3-cyclobutylamidinourea
1-[2-(3'-pyridyl)ethyl]-3-cyclohexylamidinourea
1-[2-(3'-pyridyl)ethyl]-3-benzylamidinourea
1-[2-(3'-pyridyl)ethyl]-3-methoxyethylamidinourea
1-[2-(3'-pyridyl)ethyl]-3-benzyloxyethylamidinourea
1-[2-(3'-pyridyl)ethyl]-3-methoxyethylamidinourea
1-[2-(3'-pyridyl)ethyl]-3-benzyloxyethylamidinourea
1-[2-(3'-pyridyl)ethyl]-3-phenethoxyethylamidinourea
1-[2-(3'-pyridyl)ethyl]-3-(N,N—dimethylamidino)urea
1-[2-(3'-pyridyl)ethyl]-3-(N,N—diethylamidino)urea
1-[2-(3'-pyridyl)ethyl]-3-(N,N—pentamethyleneamidino)urea
1-[2-(4'-pyridyl)ethyl]-3-methylamidinourea
1-[2-(4'-pyridyl)ethyl]-3-ethylamidinourea
1-[2-(4'-pyridyl)ethyl]-3-propylamidinourea
1-[2-(4'-pyridyl)ethyl]-3-i-propylamidinourea
1-[2-(4'-pyridyl)ethyl]-3-butylamidinourea
1-[2-(4'-pyridyl)ethyl]-3-t-butylamidinourea
1-[2-(4'-pyridyl)ethyl]-3-pentylamidinourea
1-[2-(4'-pyridyl)ethyl]-3-hexylamidinourea
1-[2-(4'-pyridyl)ethyl]-3-propargylamidinourea
1-[2-(4'-pyridyl)ethyl]-3-allylamidinourea
1-[2-(4'-pyridyl)ethyl]-3-methoxyethylamidinourea
1-[2-(4'-pyridyl)ethyl]-3-benzyloxyethylamidinourea
1-[2-(4'-pyridyl)ethyl]-3-phenethoxyethylamidinourea
1-[2-(4'-pyridyl)ethyl]-3-(N,N—dimethylamidino)urea
1-[2-(4'-pyridyl)ethyl]-3-(N,N—diethylamidino)urea
1-[2-(4'-pyridyl)ethyl]-3-(N—methyl-N—ethylamidino)urea
1-[3-(2'-pyridyl)propyl]-3-methylamidinourea
1-[3-(2'-pyridyl)propyl]-3-ethylamidinourea
1-[3-(2'-pyridyl)propyl]-3-propylamidinourea
1-[3-(2'-pyridyl)propyl]-3-i-propylamidinourea
1-[3-(2'-pyridyl)propyl]-3-butylamidinourea
1-[3-(2'-pyridyl)propyl]-3-i-butylamidinourea
1-[3-(2'-pyridyl)propyl]-3-pentylamidinourea
1-[3-(2'-pyridyl)propyl]-3-propargylamidinourea
1-[3-(2'-pyridyl)propyl]-3-allylamidinourea
1-[3-(2'-pyridyl)propyl]-3-methoxyethylamidinourea
1-[3-(2'-pyridyl)propyl]-3-benzyloxyethylamidinourea
1-[3-(2'-pyridyl)propyl]-3-phenethoxyethylamidinourea
1-[3-(2'-pyridyl)propyl]-3-(N,N—dimethylamidino)urea
1-[3-(2'-pyridyl)propyl]-3-(N,N—diethylamidino)urea
1-[3-(2'-pyridyl)propyl]-3-(N,N—tetramethyleneamidino)urea
1-[3-(2'-pyridyl)propyl]-3-(N,N—pentamethyleneamidino)urea
1-[3-(2'-pyridyl)propyl]-3-(N,N—hexamethyleneamidino)urea
1-[3-(3'-methyl-2'-pyridyl)propyl]-3-methylamidinourea
1-[3-(3'methyl-2'-pyridyl)propyl]-3-ethylamidinourea
1-[3-(3'-methyl-2'-pyridyl)propyl]-3-propylamidinourea
1-[3-(3'-methyl-2'-pyridyl)propyl]-3-i-propylamidinourea
1-[3-(3'-methyl-2'-pyridyl)propyl]-3-i-butylamidinourea
1-[3-(3'-methyl-2'-pyridyl)propyl]-3-pentylamidinourea
1-[3-(3'-methyl-2'-pyridyl)propyl]-3-allylamidinourea
1-[3-(3'-methyl-2'-pyridyl)propyl]-3-propargylamidinourea
1-[3-(3'-methyl-2'-pyridyl)propyl]-3-cyclopropylamidinourea
1-[3-(3'-methyl-2'-pyridyl)propyl]-3-methoxyethylamidinourea
1-[3-(3'-methyl-2'-pyridyl)propyl]-3-benzyloxyethylamidinourea
1-[3-(3'-methyl-2'-pyridyl)propyl]-3-phenethoxyethylamidinourea
1-[3-(3'-methyl-2'-pyridyl)propyl]-3-benzylamidinourea
1-[3-(3'-methyl-2'-pyridyl)propyl]-3-(N,N—dimethylamidino)urea
1-[3-(3'-methyl-2'-pyridyl)propyl]-3-(N,N—diethylamidino)urea
1-[3-(3'-methyl-2'-pyridyl)propyl]-3-(N,N—tetramethyleneamidino)urea
1-[3-(3'-methyl-2'-pyridyl)propyl]-3-(N,N—pentamethyleneamidino)urea
1-[3-(3'-chloro-2'-pyridyl)propyl]-3-methylamidinourea
1-[3-(3'-chloro-2'-pyridyl)propyl]-3-ethylamidinourea
1-[3-(3'-chloro-2'-pyridyl)propyl]-3-propylamidinourea
1-[3-(3'-chloro-2'-pyridyl)propyl]-3-i-propylamidinourea
1-[3-(3'-chloro-2'-pyridyl)propyl]-3-butylamidinourea
1-[3-(3'-chloro-2'-pyridyl)propyl]-3-i-butylamidinourea
1-[3-(3'-chloro-2'-pyridyl)propyl]-3-t-butylamidinourea
1-[3-(3'-chloro-2'-pyridyl)propyl]-3-pentylamidinourea
1-[3-(3'-chloro-2'-pyridyl)propyl]-3-allylamidinourea
1-[3-(3'-chloro-2'-pyridyl)propyl]-3-propargylamidinourea
1-[3-(3'-chloro-2'-pyridyl)propyl]-3-cyclopropylamidinourea
1-[3-(3'-chloro-2'-pyridyl)propyl]-3-cyclobutylamidinourea
1-[3-(3'-chloro-2'-pyridyl)propyl]-3-(N—[3'-cyclopentenyl]amidino)-urea
1-[3-(3'-chloro-2'-pyridyl)propyl]-3-cyclopropylmethylamidinourea
1-[3-(3'-chloro-2'-pyridyl)propyl]-3-methoxyethylamidinourea
1-[3-(3'-chloro-2'-pyridyl)propyl]-3-benzyloxyethylamidinourea
1-[3-(3'-chloro-2'-pyridyl)propyl]-3-phenethoxyethylamidinourea
1-[3-(3'-chloro-2'-pyridyl)propyl]-3-benzylamidinourea
1-[3-(3'-chloro-2'-pyridyl)propyl]-3-(N,N—dimethylamidino)urea
1-[3-(3'-chloro-2'-pyridyl)propyl]-3-(N,N—diethylamidino)urea
1-[3-(3'-chloro-2'-pyridyl)propyl]-3-(N,N—tetramethyleneamidino)-urea
1-[3-(2'-pyridyl)propyl]-3-(N,N[3'-methyl-3'-azapentamethylene]-amidino)urea
1-[3-(2'-pyridyl)propyl]-3-(N,N[3'-oxapentamethylene]amidino)urea
1-[3-(2'-pyridyl)propyl]-3-methylamidinourea
1-[3-(2'-pyridyl)propyl]-3-ethylamidinourea
1-[3-(2'-pyridyl)propyl]-3-propylamidinourea
1-[3-(2'-pyridyl)propyl]-3-i-propylamidinourea
1-[3-(2'-pyridyl)propyl]-3-butylamidinourea
1-[3-(2'-pyridyl)propyl]-3-i-butylamidinourea
1-[3-(3'-pyridyl)propyl]-3-t-butylamidinourea
1-[3-(3'-pyridyl)propyl]-3-pentylamidinourea
1-[3-(3'-pyridyl)propyl]-3-allylamidinourea
1-[3-(3'-pyridyl)propyl]-3-propargylamidinourea
1-[3-(3'-pyridyl)propyl]-3-cyclobutylamidinourea
1-[3-(3'-pyridyl)propyl]-3-cyclohexylamidinourea
1-[3-(3'-pyridyl)propyl]-3-benzylamidinourea
1-[3-(3'-pyridyl)propyl]-3-methoxyethylamidinourea
1-[3-(3'-pyridyl)propyl]-3-benzyloxyethylamidinourea
1-[3-(3'-pyridyl)propyl]-3-methoxyethylamidinourea
1-[3-(3'-pyridyl)propyl]-3-benzyloxyethylamidinourea
1-[3-(3'-pyridyl)propyl]-3-phenethoxyethylamidinourea
1-[3-(3'-pyridyl)propyl]-3-(N,N—dimethylamidino)urea
1-[3-(3'-pyridyl)propyl]-3-(N,N—diethylamidino)urea
1-[3-(3'-pyridyl)propyl]-3-(N,N—pentamethyleneamidino)urea
1-[3-(4'-pyridyl)propyl]-3-methylamidinourea
1-[3-(4'-pyridyl)propyl]-3-ethylamidinourea
1-[3-(4'-pyridyl)propyl]-3-propylamidinourea
1-[3-(4'-pyridyl)propyl]-3-i-propylamidinourea
1-[3-(4'-pyridyl)propyl]-3-butylamidinourea
1-[3-(4'-pyridyl)propyl]-3-t-butylamidinourea
1-[3-(4'-pyridyl)propyl]-3-pentylamidinourea
1-[3-(4'-pyridyl)propyl]-3-hexylamidinourea
1-[3-(4'-pyridyl)propyl]-3-propargylamidinourea
1-[3-(4'-pyridyl)propyl]-3-allylamidinourea
1-[3-(4'-pyridyl)propyl]-3-methoxyethylamidinourea
1-[3-(4'-pyridyl)propyl]-3-benzyloxyethylamidinourea
1-[3-(4'-pyridyl)propyl]-3-phenethoxyethylamidinourea
1-[3-(4'-pyridyl)propyl]-3-(N,N—dimethylamidino)urea
1-[3-(4'-pyridyl)propyl]-3-(N,N—diethylamidino)urea
1-[3-(4'-pyridyl)propyl]-3-(N—methyl-N—ethylamidino)urea

TABLE I-a

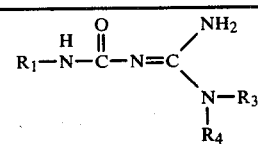

| $R_1$ | $R_3$ | $R_4$ |
|---|---|---|
| ![pyridyl-CH2] | H | H |
| ![pyridyl-CH2] | H | —CH$_3$ |
| ![pyridyl-CH2] | H | —C$_2$H$_5$ |

TABLE I-a-continued $$R_1-\overset{H}{N}-\overset{O}{\underset{\|}{C}}-N=\overset{NH_2}{\underset{\underset{R_4}{|}}{C}}-N-R_3$$

| $R_1$ | $R_3$ | $R_4$ |
|---|---|---|
| (pyridin-2-yl)-CH₂– | –CH₃ | –CH₃ |
| (pyridin-2-yl)-CH₂– | H | –OCH₃ |
| (3-methylpyridin-2-yl)-CH₂– | H | –CH₃ |
| (3-methylpyridin-2-yl)-CH₂– | –CH₃ | –CH₃ |
| (3-methylpyridin-2-yl)-CH₂– | –C₂H₅ | –C₂H₅ |
| (2,4-dimethyl-pyridin-3-yl)-CH₂– | H | H |
| (2,4-dimethyl-pyridin-3-yl)-CH₂– | H | –CH₃ |
| (2,4-dimethyl-pyridin-3-yl)-CH₂– | H | –C₂H₅ |
| (2,4-dimethyl-pyridin-3-yl)-CH₂– | H | –OCH₃ |
| (3,5-dimethyl-pyridin-4-yl)-CH₂– | | |
| (3,5-dimethyl-pyridin-4-yl)-CH₂– | –CH₃ | –CH₃ |
| (3,5-dimethyl-pyridin-4-yl)-CH₂– | –CH₃ | –C₂H₅ |
| (3-ethylpyridin-2-yl)-CH₂– | H | H |
| (3-ethylpyridin-2-yl)-CH₂– | H | –CH₃ |
| (3-ethylpyridin-2-yl)-CH₂– | H | –C₂H₅ |
| (4,6-dimethylpyrimidin-5-yl)-CH₂– | –CH₃ | –CH₃ |
| (4,6-dimethylpyrimidin-5-yl)-CH₂– | H | –C₂H₅ |
| (pyridin-4-yl)-CH₂– | H | H |
| (pyridin-4-yl)-CH₂– | H | –CH₃ |

TABLE I-a-continued
$$R_1-\overset{H}{N}-\overset{O}{\underset{\|}{C}}-N=\overset{NH_2}{\underset{\underset{R_4}{|}}{C}}-N-R_3$$
| $R_1$ | $R_3$ | $R_4$ |
|---|---|---|
| 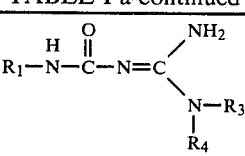 | H | H |
| 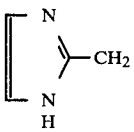 | H | —CH₃ |
| 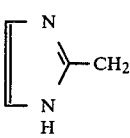 | H | —C₂H₅ |
| 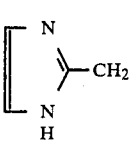 | H | H |
| 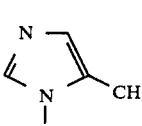 | H | —CH₃ |
| 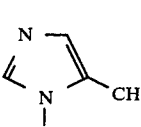 | H | H |
| 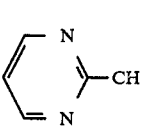 | H | —CH₃ |
| 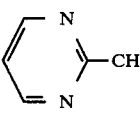 | —CH₃ | —CH₃ |
| 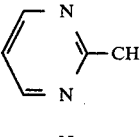 | —H | —CH₃ |
| 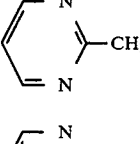 | —H | —C₂H₅ |
| 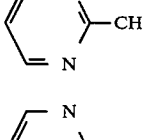 | —CH₃ | —CH₃ |
| 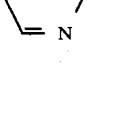 | H | H |
|  | H | —CH₃ |
| 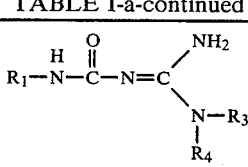 | H | —CH₃ |
| 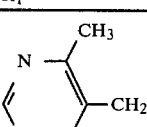 | H | H |
| 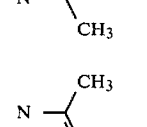 | H | —CH₃ |
| 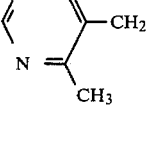 | H | —C₂H₅ |
| 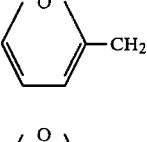 | H | —CH₃ |
| 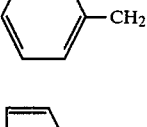 | —CH₃ | —CH₃ |
| 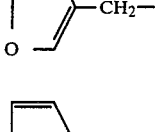 | —H | —CH₃ |
| 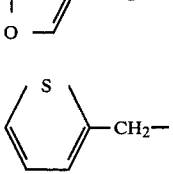 | —H | —C₂H₅ |

TABLE I-a-continued
$$R_1-\overset{H}{N}-\overset{O}{\underset{\|}{C}}-N=\overset{NH_2}{\underset{\underset{R_4}{|}}{C}}-N-R_3$$
| R₁ | R₃ | R₄ |
|---|---|---|
| 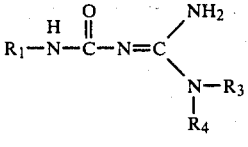 | —H | —CH₃ |
| 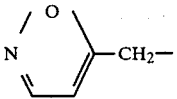 | H | —CH₃ |
| 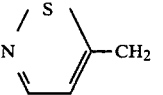 | H | —C₂H₅ |
| 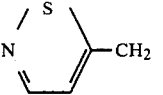 | H | —CH₃ |
| 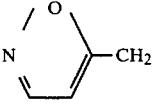 | H | —CH₃ |
| 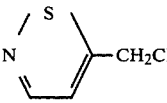 | H | —C₂H₅ |
| 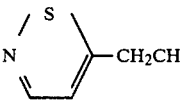 | H | —CH₃ |
| 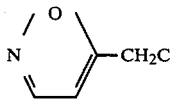 | H | H |
| 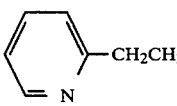 | H | —CH₃ |
| 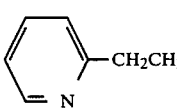 | H | —C₂H₅ |
| 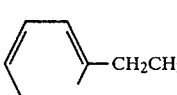 | —CH₃ | —CH₃ |
| 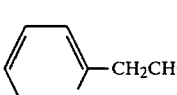 | H | —OCH₃ |
| 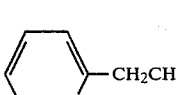 | H | —CH₃ |
|  | —CH₃ | —CH₃ |
| 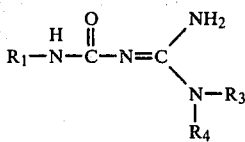 | —C₂H₅ | —C₂H₅ |
| 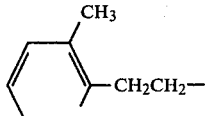 | H | H |
| 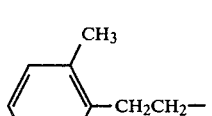 | H | —CH₃ |
| 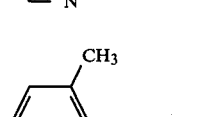 | H | —C₂H₅ |
| 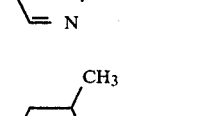 | H | —OCH₃ |
| 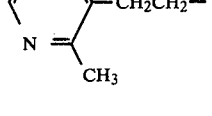 | —CH₃ | —CH₃ |

TABLE I-a-continued $$R_1-\overset{H}{N}-\overset{O}{\underset{}{C}}-N=\overset{NH_2}{\underset{\underset{R_4}{N-R_3}}{C}}$$

| R₁ | R₃ | R₄ |
|---|---|---|
| 3,5-dimethyl-4-pyridyl-CH₂CH₂— | —CH₃ | —C₂H₅ |
| 3-ethyl-2-pyridyl-CH₂CH₂— | H | H |
| 3-ethyl-2-pyridyl-CH₂CH₂— | H | —CH₃ |
| 3-ethyl-2-pyridyl-CH₂CH₂— | H | —C₂H₅ |
| 4,6-dimethyl-5-pyrimidinyl-CH₂CH₂— | —CH₃ | —CH₃ |
| 4,6-dimethyl-5-pyrimidinyl-CH₂CH₂— | H | —C₂H₅ |
| 4-pyridyl-CH₂CH₂— | H | H |
| 4-pyridyl-CH₂CH₂— | H | —CH₃ |
| 2-(1H-imidazol-2-yl)-CH₂CH₂— | H | H |
| 2-(1H-imidazol-2-yl)-CH₂CH₂— | H | —CH₃ |
| 2-(1H-imidazol-2-yl)-CH₂CH₂— | H | —C₂H₅ |
| 5-(1H-imidazol-4-yl)-CH₂CH₂— | H | H |
| 5-(1H-imidazol-4-yl)-CH₂CH₂— | H | —CH₃ |
| 2-pyrimidinyl-CH₂CH₂— | H | H |
| 2-pyrimidinyl-CH₂CH₂— | H | —CH₃ |
| 2-pyrimidinyl-CH₂CH₂— | —CH₃ | —CH₃ |
| 2-pyrimidinyl-CH₂CH₂— | —H | —CH₃ |
| 2-pyrimidinyl-CH₂CH₂— | —H | —C₂H₅ |
| 2-pyrimidinyl-CH₂CH₂— | —CH₃ | —CH₃ |

TABLE I-a-continued $$R_1-N(H)-C(=O)-N=C(NH_2)(N(R_3)(R_4))$$

| R₁ | R₃ | R₄ |
|---|---|---|
| 4,6-dimethylpyrimidin-5-yl-CH₂CH₂— | H | H |
| 4,6-dimethylpyrimidin-5-yl-CH₂CH₂— | H | —CH₃ |
| 2H-pyran-3-yl-CH₂CH₂— | H | —CH₃ |
| 2H-pyran-3-yl-CH₂—CH₂— | H | H |
| furan-3-yl-CH₂—CH₂— | H | —CH₃ |
| furan-3-yl-CH₂—CH₂— | H | —C₂H₅ |
| thiopyran-3-yl-CH₂—CH₂— | H | —CH₃ |
| thiopyran-3-yl-CH₂—CH₂— | —CH₃ | —CH₃ |
| 1H-pyridin-3-yl-CH₂—CH₂— | —H | —CH₃ |
| 1H-pyridin-3-yl-CH₂—CH₂— | —H | —C₂H₅ |
| isoxazol-5-yl-CH₂—CH₂— | —H | —CH₃ |

TABLE II 1-(2-pyridylmethyl)-4-methylamino-1,2-dihydro-1,3,5-triazin-2-one
1-(2-pyridylmethyl)-4-ethylamino-1,2-dihydro-1,3,5-triazin-2-one
1-(2-pyridylmethyl)-4-propylamino-1,2-dihydro-1,3,5,-triazin-2-one
1-(2-pyridylmethyl)-4-i-propylamino-1,2-dihydro-1,3,5-triazin-2-one
1-(2-pyridylmethyl)-4-butylamino-1,2-dihydro-1,3,5-triazin-2-one
1-(2-pyridylmethyl)-4-i-butylamino-1,2-dihydro-1,3,5-triazin-2-one
1-(2-pyridylmethyl)-4-t-butylamino-1,2-dihydro-1,3,5-triazin-2-one
1-(2-pyridylmethyl)-4-pentylamino-1,2-dihydro-1,3,5-triazin-2-one
1-(2-pyridylmethyl)-4-allylamino-1,2-dihydro-1,3,5-triazin-2-one
1-(2-pyridylmethyl)-4-propargylamino-1,2-dihydro-1,3,5-triazin-2-one
1-(2-pyridylmethyl)-4-cyclopropylamino-1,2-dihydro-1,3,5-triazin-2-one
1-(2-pyridylmethyl)-4-methoxyethylamino-1,2-dihydro-1,3,5-triazin-2-one.
1-(2-pyridylmethyl)-4-benzyloxyethylamino-1,2-dihydro-1,3,5-triazin-2-one
1-(2-pyridylmethyl)-4-phenethoxyethylamino-1,2-dihydro-1,3,5-triazin-2-one
1-(2-pyridylmethyl)-4-benzylamino-1,2-dihydro-1,3,5-triazin-2-one
1-(2-pyridylmethyl)-4-(N,N—dimethylamino)-1,2-dihydro-1,3,5-triazin-2-one
1-(2-pyridylmethyl)-4-(N,N—diethylamino)-1,2-dihydro-1,3,5-triazin-2-one
1-(2-pyridylmethyl)-4-(N—pyrrolidinyl)-1,2-dihydro-1,3,5-triazin-2-one
1-(2-pyridylmethyl)-4-(N—piperidyl)-1,2-hydro-1,3,5-triazin-2-one
1-(3-methyl-2-pyridylmethyl)-4-methylamino-1,2-dihydro-1,3,5-triazin-2-one
1-(3-methyl-2-pyridylmethyl)-4-ethylamino-1,2-dihydro-1,3,5-triazin-2-one
1-(3-methyl-2-pyridylmethyl)-4-propylamino-1,2-hydro-1,3,5-triazin-2-one
1-(3-methyl-2-pyridylmethyl)-4-i-propylamino-1,2-dihydro-1,3,5-triazin-2-one
1-(3-methyl-2-pyridylmethyl)-4-butylamino-1,2-dihydro-1,3,5-triazin-2-one
1-(3-methyl-2-pyridylmethyl)-4-i-butylamino-1,2-dihydro-1,3,5-triazin-2-one
1-(3-methyl-2-pyridylmethyl)-4-t-butylamino-1,2-dihydro-1,3,5-triazin-2-one
1-(3-methyl-2-pyridylmethyl)-4-pentylamino-1,2-dihydro-1,3,5-triazin-2-one
1-(3-methyl-2-pyridylmethyl)-4-allylamino-1,2-dihydro-1,3,5-triazin-2-one
1-(3-methyl-2-pyridylmethyl)-4-proparagylamino-1,2-dihydro-1,3,5-triazin-2-one
1-(3-methyl-2-pyridylmethyl)-4-cyclopropylamino-1,2-dihydro-1,3,5-triazin-2-one
1-(3-methyl-2-pyridylmethyl)-4-cyclobutylamino-1,2-dihydro-1,3,5-triazin-2-one
1-(3-methyl-2-pyridylmethyl)-4-cyclopenten-3-yl-amino-1,3,5-triazin-2-one

TABLE II-continued 1-(3-methyl-2-pyridylmethyl)-4-cyclopropylmethylamino-1,2-dihydro-1,3,5-triazin-2-one
1-(3-methyl-2-pyridylmethyl)-4-methoxyethylamino-1,2-dihydro-1,3,5-triazin-2-one
1-(3-methyl-2-pyridylmethyl)-4-benzyloxyethylamino-1,2-dihydro-1,3,5-triazin-2-one
1-(3-methyl-2-pyridylmethyl)-4-phenethoxyethylamino-1,2-dihydro-1,3,5-triazin-2-one
1-(3-methyl-2-pyridylmethyl)-4-benzylamino-1,2-dihydro-1,3,5-triazin-2-one
1-(3-methyl-2-pyridylmethyl)-4-(N,N—dimethylamino-)-1,2-dihydro-1,3,5-triazin-2-one
1-(3-methyl-2-pyridylmethyl)-4-(N,N—diethylamino-)-1,2-dihydro-1,3,5-triazin-2-one
1-(3-methyl-2-pyridylmethyl)-4-(N—pyrrolidinyl)-1,2-dihydro-1,3,5-triazin-2-one
1-(3-methyl-2-pyridylmethyl)-4-[3-(N—methyl-piperidyl)]-1,2-dihydro-1,3,5-triazin-2-one
1-(3-chloro-2-pyridylmethyl)-4-methylamino-1,2-dihydro-1,3,5-triazin-2-one
1-(3-chloro-2-pyridylmethyl)-4-(N—morpholinyl)-1,2-dihydro-1,3,5-triazin-2-one
1-(3-chloro-2-pyridylmethyl)-4-ethylamino-1,2-dihydro-1,3,5-triazin-2-one
1-(3-chloro-2-pyridylmethyl)-4-propylamino-1,2-dihydro-1,3,5-triazin-2-one
1-(3-chloro-2-pyridylmethyl)-4-i-propylamino-1,2-dihydro-1,3,5-triazin-2-one
1-(3-chloro-2-pyridylmethyl)-4-butylamino-1,2-dihydro-1,3,5-triazin-2-one
1-(3-chloro-2-pyridylmethyl)-4-i-butylamino-1,2-dihydro-1,3,5-triazin-2-one
1-(3-chloro-2-pyridylmethyl)-4-t-butylamino-1,2-dihydro-1,3,5-triazin-2-one
1-(3-chloro-2-pyridylmethyl)-4-pentylamino-1,2-dihydro-1,3,5-triazin-2-one
1-(3-chloro-2-pyridylmethyl)-4-propargylamino-1,2-dihydro-1,3,5-triazin-2-one
1-(3-chloro-2-pyridylmethyl)-4-cyclobutylamino-1,2-dihydro-1,3,5-triazin-2-one
1-(3-chloro-2-pyridylmethyl)-4-cyclohexylamino-1,2-dihydro-1,3,5-triazin-2-one
1-(3-chloro-2-pyridylmethyl)-4-benzylamino-1,2-dihydro-1,3,5-triazin-2-one
1-(3-chloro-2-pyridylmethyl)-4-methoxyethylamino-1,2-dihydro-1,3,5-triazin-2-one
1-(3-chloro-2-pyridylmethyl)-4-benzyloxyethylamino-1,2-dihydro-1,3,5-triazin-2-one
1-(3-chloro-2-pyridylmethyl)-4-phenethoxyethylamino-1,2-dihydro-1,3,5-triazin-2-one
1-(3-chloro-2-pyridylmethyl)-4-(N,N—diethylamino)-1,2-dihydro-1,3,5-triazin-2-one
1-(3-chloro-2-pyridylmethyl)-4-(N—piperidinyl)-1,2-dihydro-1,3,5-triazin-2-one
1-(3-pyridylmethyl)-4-methylamino-1,2-dihydro-1,3,5-triazin-2-one
1-(3-pyridylmethyl)-4-ethylamino-1,2-dihydro-1,3,5-triazin-2-one
1-(3-pyridylmethyl)-4-propylamino-1,2-dihydro-1,3,5-triazin-2-one
1-(3-pyridylmethyl)-4-i-propylamino-1,2-dihydro-1,3,5-triazin-2-one
1-(3-pyridylmethyl)-4-butylamino-1,2-dihydro-1,3,5-triazin-2-one
1-(3-pyridylmethyl)-4-t-butylamino-1,2-dihydro-1,3,5-triazin-2-one
1-(3-pyridylmethyl)-4-pentylamino-1,2-dihydro-1,3,5-triazin-2-one
1-(3-pyridylmethyl)-4-hexylamino-1,2-dihydro-1,3,5-triazin-2-one
1-(3-pyridylmethyl)-4-propargylamino-1,2-dihydro-1,3,5-triazin-2-one
1-(3-pyridylmethyl)-4-allylamino-1,2-dihydro-1,3,5-triazin-2-one
1-(3-pyridylmethyl)-4-methoxyethylamino-1,2-dihydro-1,3,5-triazin-2-one
1-(3-pyridylmethyl)-4-benzyloxyethylamino-1,2-dihydro-1,3,5-triazin-2-one
1-(3-pyridylmethyl)-4-phenethoxyethylamino-1,2-dihydro-1,3,5-triazin-2-one
1-(3-pyridylmethyl)-4-(N,N—dimethylamino)-1,2-dihydro-1,3,5-triazin-2-one
1-(3-pyridylmethyl)-4-(N,N—diethylamino)-1,2-dihydro-1,3,5-triazin-2-one
1-(3-pyridylmethyl)-4-(N—methyl-N—ethylamino)-1,2-dihydro-1,3,5-triazin-2-one
1-(3-pyridylmethyl)-4-(N—pyrrolidyl)-1,2-dihydro-1,3,5-triazin-2-one
1-(3-pyridylmethyl)-4-(N—piperidyl-1,2-dihydro-1,3,5-triazin-2-one
1-(3-pyridylmethyl)-4-(N—azipinyl)-1,2-dihydro-1,3,5-triazin-2-one
1-(4-pyridylmethyl)-4-methylamino-1,2-dihydro-1,3,5-triazin-2-one
1-(4-pyridylmethyl)-4-ethylamino-1,2-dihydro-1,3,5-triazin-2-one
1-(4-pyridylmethyl)-4-propylamino-1,2-dihydro-1,3,5-triazin-2-one
1-(4-pyridylmethyl)-4-butylamino-1,2-dihydro-1,3,5-triazin-2-one
1-(4-pyridylmethyl)-4-i-butylamino-1,2-dihydro-1,3,5-triazin-2-one
1-(4-pyridylmethyl)-4-pentylamino-1,2-dihydro-1,3,5-triazin-2-one
1-(4-pyridylmethyl)-4-allylamino-1,2-dihydro-1,3,5-triazin-2-one
1-(4-pyridylmethyl)-4-propargylamino-1,2-dihydro-1,3,5-triazin-2-one
1-(4-pyridylmethyl)-4-methoxyethylamino-1,2-dihydro-1,3,5-triazin-2-one
1-(4-pyridylmethyl)-4-benzyloxyethylamino-1,2-dihydro-1,3,5-triazin-2-one
1-(4-pyridylmethyl)-4-(N,N—dimethylamino)-1,2-dihydro-1,3,5-triazin-2-one
1-(4-pyridylmethyl)-4-(N,N—diethylamino)-1,2-dihydro-1,3,5-triazin-2-one
1-(4-pyridylmethyl)-4-(N—pyrrolidinyl)-1,2-dihydro-1,3,5-triazin-2-one
1-(2-methyl-4-fluoro-3-pyridylmethyl)-4-methylamino-1,2-dihydro-1,3,5-triazin-2-one
1-(2,4-dimethyl-3-pyridylmethyl)-4-methylamino-1,2-dihydro-1,3,5-triazin-2-one
1-(2,4-diethyl-3-pyridylmethyl)-4-methylamino-1,2-dihydro-1,3,5-triazin-2-one
1-(2-methyl-4-chloro-3-pyridylmethyl)-4-methylamino-1,2-dihydro-1,3,5-triazin-2-one
1-(2-methyl-4-bromo-3-pyridylmethyl)-4-methylamino-1,2-dihydro-1,3,5-triazin-2-one
1-(2-methyl-4-fluoro-3-pyridylethyl)-4-methylamino-1,2-hydro-1,3,5-triazin-2-one
1-(2-methyl-4-ethyl-3-pyridylmethyl)-4-methylamino-1,2-dihydro-1,3,5-triazin-2-one
1-(2-ethyl-4-chloro-3-pyridylmethyl)-4-methylamino-1,2-dihydro-1,3,5-triazin-2-one
1-(2-ethyl-4-bromo-3-pyridylmethyl)-4-methylamino-1,2-dihydro-1,3,5-triazin-2-one
1-(2-ethyl-4-fluoro-3-pyridylethyl)-4-methylamino-1,2-dihydro-1,3,5-triazin-2-one
1-(2,4-dimethyl-3-pyridylethyl)-4-methylamino-1,2-dihydro-1,3,5-triazin-2-one
1-(2,6-diethyl-4-pyridylmethyl)-4-methylamino-1,2-dihydro-1,3,5-triazin-2-one
1-[2-(2-methyl-6-ethyl-4-pyridyl)ethyl]-4-methylamino-1,2-dihydro-1,3,5-triazin-2-one
1-(2-thiophenylmethyl)-4-methylamino-1,2-dihydro-1,3,5-triazin-2-one
1-(3-thiophenylmethyl)-4-methylamino-1,2-dihydro-1,3,5-triazin-2-one
1-[2-(2-thiophenyl)ethyl]-4-methylamino-1,2-dihydro-1,3,5-triazin-2-one
1-[3-(2-thiophenyl)propyl]-4-methylamino-1,2-dihydro-1,3,5-triazin-2-one
1-[2-(3-thiophenyl)ethyl]-4-methylamino-1,2-dihydro-1,3,5-triazin-2-one
1-(5-ethyl-2-thiophenylmethyl)-4-methylamino-1,2-dihydro-1,3,5-triazin-2-one
1-(5-chloro-2-thiophenylmethyl)-4-methylamino-1,2-dihydro-1,3,5-triazin-2-one
1-(3-cyano-2-pyridylmethyl)-4-methylamino-1,2-dihydro-1,3,5-triazin-2-one
1-(3-carbomethoxy-2-pyridylmethyl)-4-methylamino-1,2-dihydro-1,3,5-triazin-2-one
1-(3-carboethoxy-2-pyridylmethyl)-4-methylamino-1,2-dihydro-1,3,5-triazin-2-one

TABLE II-continued 1-(3-methyl-2-pyridylmethyl-4-methylamino-1,2-dihydro-1,3,5-triazin-2-one
1-(2-methyl-3-pyridylmethyl)-4-methylamino-1,2-dihydro-1,3,5-triazin-2-one
1-(2-ethyl-3-pyridylmethyl)-4-methylamino-1,2-hydro-1,3,5-triazin-2-one
1-(2,6-dimethyl-3-pyridylmethyl)-4-methylamino-1,2-hydro-1,3,5-triazin-2-one
1-(2-ethyl-6-bromo-3-pyridylmethyl)-4-methylamino-1,2-dihydro-1,3,5-triazin-2-one
1-(2-ethyl-6-fluoro-3-pyridylmethyl)-4-methylamino-1,2-dihydro-1,3,5-triazin-2-one
1-(3-cyano-2-thiophenylmethyl)-4-methylamino-1,2-dihydro-1,3,5-triazin-2-one
1-(3-carbomethoxy-2-thiophenylmethyl)-4-methylamino-1,2-dihydro-1,3,5-triazin-2-one
1-(3-carboethoxy-2-thiophenylmethyl)-4-methylamino-1,2-dihydro-1,3,5-triazin-2-one
1-(2-methoxy-3-pyridylmethyl)-4-(N,N—diethylamino)-1,2-dihydro-1,3,5-triazin-2-one
1-(2-ethoxy-3-pyridylmethyl)-4-(N—ethyl-N—methylamino)-1,2-dihydro-1,3,5-triazin-2-one
1-(2-chloro-3-pyridylmethyl)-4-(N—methyl-N—propylamino)-1,2-dihydro-1,3,5-triazin-2-one
1-furfuryl-4-(N—methyl-N—butylamino)-1,2-dihydro-1,3,5-triazin-2-one
1-furfuryl-4-(N,N—dipropylamino)-1,2-dihydro-1,3,5-triazin-2-one
1-furfuryl-4-(N—ethyl-N—propylamino)-1,2-dihydro-1,3,5-triazin-2-one
1-furfuryl-4-(N—methyl-N—benzyloxypropylamino)-1,2-dihydro-1,3,5-triazin-2-one
1-furfuryl-4-(N—methyl-N—phenethoxyethylamino)-1,2-dihydro-1,3,5-triazin-2-one
1-furfuryl-4-(N—methyl-N—benzyloxyethylamino)-1,2-dihydro-1,3,5-triazin-2-one
1-furfuryl-4-(N—pyrrolidinyl)-1,2-dihydro-1,3,5-triazin-2-one
1-furfuryl-4-(N—piperidyl)-1,2-dihydro-1,3,5-triazin-2-one
1-furfuryl-4-(N—azipinyl)-1,2-dihydro-1,3,5-triazin-2-one
1-furfuryl-4-(N—morpholinyl)-1,2-dihydro-1,3,5-triazin-2-one
1-furfuryl-4-[3-(N—methylpiperidyl)]-1,2-dihydro-1,3,5-triazin-2-one
1-furfuryl-4-[3-(N—methyl azipinyl)]-1,2-dihydro-1,3,5-triazinone
1-furfuryl-4-[N—(3-thiomorpholinyl)]-1,2-dihydro-1,3,5-triazin-2-one
1-furfuryl-4-[N—(1-thioazolinyl)]-1,2-dihydro-1,3,5-triazin-2-one
1-furfuryl-4-(2-butenylamino)-1,2-dihydro-1,3,5-triazin-2-one
1-furfuryl-4-(2-butylnylamino)-1,2-dihydro-1,3,5-triazin-2-one
1-furfuryl-4-(3-butylnylamino)-1,2-dihydro-1,3,5-triazin-2-one
1-furfuryl-4-(N—methyl-N—allylamino)-1,2-dihydro-1,3,5-triazin-2-one
1-furfuryl-4-(N—methyl-N—propargylamino)-1,2-hydro-1,3,5-triazin-2-one
1-furfuryl-4-(N—methyl-N—cyclopropylamino)-1,2-dihydro-1,3,5-triazin-2-one
1-furfuryl-4-methylamino-1,2-dihydro-1,3,5-triazin-2-one
1-furfuryl-4-(N,N—dimethylamino)-1,2-dihydro-1,3,5-triazin-2-one
1-tetrahydrofurfuryl-4-methylamino-1,2-dihydro-1,3,5-triazin-2-one
1-tetrahydrofurfuryl-4-methylamino-1,2-dihydro-1,3,5-triazin-2-one
1-(1-imidazolylmethyl)-4-methylamino-1,2-dihydro-1,3,5-triazin-2-one
1-(2-imidazolylmethyl)-4-methylamino-1,2-dihydro-1,3,5-triazin-2-one
1-(4-imidazolylmethyl)-4-methylamino-1,2-dihydro-1,3,5-triazin-2-one
1-(2-oxazolylmethyl)-4-methylamino-1,2-dihydro-1,3,5-triazin-2-one
1-(4-oxazolylmethyl)-4-methylamino-1,2-dihydro-1,3,5-triazin-2-one
1-(5-oxazolylmethyl)-4-methylamino-1,2-dihydro-1,3,5-triazin-2-one
1-(2-thiazolylmethyl)-4-methylamino-1,2-dihydro-1,3,5-triazin-2-one
1-(4-thiazolylmethyl)-4-methylamino-1,2-dihydro-1,3,5-triazin-2-one
1-(5-thiazolylmethyl)-4-methylamino-1,2-dihydro-1,3,5-triazin-2-one
1-(1-pyrazolylmethyl)-4-methylamino-1,2-dihydro-1,3,5-triazin-2-one
1-(1-[3-pyrrolidinyl]methyl)-4-methylamino-1,2-dihydro-1,3,5-triazin-2-one
1-(2-pyrrolidinylmethyl)-4-methylamino-1,2-dihydro-1,3,5-triazin-2-one
1-(1-morpholinylmethyl)-4-methylamino-1,2-dihydro-1,3,5-triazin-2-one
1-(2-morpholinylmethyl)-4-methylamino-1,2-dihydro-1,3,5-triazin-2-one
1-(2-pyrimidinylmethyl)-4-methylamino-1,2-dihydro-1,3,5-triazin-2-one
1-(4-pyrimidinylmethyl)-4-methylamino-1,2-dihydro-1,3,5-triazin-2-one
1-(2-quinolinylmethyl)-4-methylamino-1,2-dihydro-1,3,5-triazin-2-one
1-(4-quinolinylmethyl)-4-methylamino-1,2-dihydro-1,3,5-triazin-2-one
1-(1-isoquinolinylmethyl)-4-methylamino-1,2-dihydro-triazin-2-one
1-(2-dihydroindolinylmethyl)-4-methylamino-1,2-dihydro-1,3,5-triazin-2-one
1-furfuryl-4-ethylamino-1,2-dihydro-1,3,5-triazin-2-one
1-furfuryl-4-propylamino-1,2-dihydro-1,3,5-triazin-2-one
1-furfuryl-4-i-propylamino-1,2-dihydro-1,3,5-triazin-2-one
1-furfuryl-4-butylamino-1,2-dihydro-1,3,5-triazin-2-one
1-furfuryl-4-(i-butylamino)-1,2-dihydro-1,3,5-triazin-2-one
1-(2-pyridylmethyl)-4-(sec-butylamino)-1,2-dihydro-1,3,5-triazin-2-one
1-(2-pyridylmethyl)-4-(t-butylamino)-1,2-dihydro-1,3,5-triazin-2-one
1-(2-pyridylmethyl)-4-pentylamino-1,2-dihydro-1,3,5-triazin-2-one
1-(2-pyridylmethyl)-4-hexylamino-1,2-dihydro-1,3,5-triazin-2-one
1-(2-pyridylmethyl)-4-heptylamino-1,2-dihydro-1,3,5-triazin-2-one
1-(2-pyridylmethyl)-4-cyclopropylamino-1,2-dihydro-1,3,5-triazin-2-one
1-(2-pyridylmethyl)-4-cyclobutylamino-1,2-dihydro-1,3,5-triazin-2-one
1-(2-pyridylmethyl)-4-cyclopentylamino-1,2-dihydro-1,3,5-triazin-2-one
1-(2-pyridylmethyl)-4-cyclohexylamino-1,2-dihydro-1,3,5-triazin-2-one
1-(2-pyridylmethyl)-4-anilino-1,2-dihydro-1,3,5-triazin-2-one
1-(2-pyridylmethyl)-4-benzylamino-1,2-dihydro-1,3,5-triazin-2-one
1-(2-pyridylmethyl)-4-phenethylamino-1,2-dihydro-1,3,5-triazin-2-one
1-(2-pyridylmethyl)-4-(N—methyl-N—benzylamino)-1,2-dihydro-1,3,5-triazin-2-one
1-(2-pyridylmethyl)-4-(N,N—dibenzylamino)-1,2-dihydro-1,3,5-triazin-2-one
1-(3-methyl-tetrahydrofurfuryl)-4-amino-1,2-dihydro-1,3,5-triazin-2-one
1-tetrohydrofurfuryl-4-amino-1,2-dihydro-1,3,5-triazin-2-one
1-(2-methyl-tetrahydrofurfuryl)-4-amino-1,2-dihydro-1,3,5-triazin-2-one
1-(1-imidazolylmethyl)-4-amino-1,2-dihydro-1,3,5-triazin-2-one
1-(2-methyl-1-imidazolylmethyl)-4-amino-1,2-dihydro-1,3,5-triazin-2-one
1-(4-imidazolylmethyl)-4-amino-1,2-dihydro-1,3,5-triazin-2-one
1-(1-methyl-4-imidazolylmethyl)-4-amino-1,2-dihydro-1,3,5-triazin-2-one

TABLE II-continued 1-(2-methyl-4-imidazolylmethyl)-4-amino-1,2-dihydro-1,3,5-triazin-2-one
1-(2-imidazolylmethyl)-4-amino-1,2-dihydro-1,3,5-triazin-2-one
1-(2-oxazolylmethyl)-4-amino-1,2-dihydro-1,3,5-triazin-2-one
1-(4-methyl-2-oxazolylmethyl)-4-amino-1,2-dihydro-1,3,5-triazin-2-one
1-(4-oxazolylmethyl)-4-amino-1,2-dihydro-1,3,5-triazin-2-one
1-(2-methyl-4-oxazolylmethyl)-4-amino-1,2-dihydro-1,3,5-triazin-2-one
1-(5-oxazolylmethyl)-4-amino-1,2-dihydro-1,3,5-triazin-2-one
1-(2-methyl-5-oxazolylmethyl)-4-amino-1,2-dihydro-1,3,5-triazin-2-one
1-(4-thiazolylmethyl)-4-amino-1,2-dihydro-1,3,5-triazin-2-one
1-(5-methyl-4-thiazolylmethyl)-4-amino-1,2-dihydro-1,3,5-triazin-2-one
1-(5-thiazolylmethyl)-4-amino-1,2-dihydro-1,3,5-triazin-2-one
1-(4-methyl-5-thiazolylmethyl)-4-amino-1,2-dihydro-1,3,5-triazin-2-one
1-(1-pyrazolylmethyl)-4-amino-1,2-dihydro-1,3,5-triazin-2-one
1-(1-[3-pyrrolidinyl]methyl)-4-amino-1,2-dihydro-1,3,5-triazin-2-one
1-(2-[3-pyrrolidinyl]methyl)-4-amino-1,2-dihydro-1,3,5-triazin-2-one
1-(1-[2-methyl-3-pyrrolidinyl]methyl)-4-amino-1,2-dihydro-1,3,5-triazin-2-one
1-(1-[3-methyl-2-pyrrolidinyl]methyl)-4-amino-1,2-dihydro-1,3,5-triazin-2-one
1-(1-pyrrolidinyl)-4-amino-1,2-dihydro-1,3,5-triazin-2-one
1-(1-methyl-2-pyrrolidinylmethyl)-4-amino-1,2-diydro-1,3,5-triazin-2-one
1-(1-morpholinylmethyl)-4-amino-1,2-dihydro-1,3,5-triazin-2-one
1-(2-methyl-1-morpholinylmethyl)-4-amino-1,2-dihydro-1,3,5-triazin-2-one
1-(2-morpholinylmethyl)-4-amino-1,2-dihydro-1,3,5-triazin-2-one
1-(1-methyl-2-morpholinylmethyl)-1,2-dihydro-1,3,5-triazin-2-one
1-(3-methyl-2-morpholinylmethyl)-4-amino-1,2-dihydro-1,3,5-triazin-2-one
1-(3-methyl-1-morpholinylmethyl)-4-amino-1,2-dihydro-1,3,5-triazin-2-one
1-(3-morpholinylmethyl)-4-amino-1,2-dihydro-1,3,5-triazin-2-one
1-(1-methyl-3-morpholinylmethyl)-4-amino-1,2-dihydro-1,3,5-triazin-2-one
1-(2-methyl-3-morpholinylmethyl)-4-amino-1,2-dihydro-1,3,5-triazin-2-one
1-(2-pyrimidinylmethyl)-4-amino-1,2-dihydro-1,3,5-triazin-2-one
1-(4-methyl-2-pyrimidinylmethyl)-4-amino-1,2-dihydro-1,3,5-triazin-2-one
1-(4-pyrimidinylmethyl)-4-amino-1,2-dihydro-1,3,5-triazin-2-one
1-(2-methyl-4-pyrimidinylmethyl)-4-amino-1,2-dihydro-1,3,5-triazin-2-one
1-(2-quinolinylmethyl)-4-amino-1,2-dihydro-1,3,5-triazin-2-one
1-(3-methyl-2-quinolinylmethyl)-4-amino-1,2-dihydro-1,3,5-triazin-2-one
1-(4-quinolinylmethyl)-4-amino-1,2,-dihydro-1,3,5-triazin-2-one
1-(2-methyl-4-quinolinylmethyl)-4-amino-1,2-dihydro-1,3,5-triazin-2-one
1-(3-methyl-4-quinolinylmethyl)-4-amino-1,2-dihydro-1,3,5-triazin-2-one
1-(1-isoquinolinylmethyl)-4-amino-1,2-dihydro-1,3,5-triazin-2-one

TABLE II-a $$R_1-N \begin{array}{c} CH=N \\ | \quad\quad | \\ C-N \\ \| \\ O \end{array} N \begin{array}{c} R_3 \\ R_4 \end{array}$$

| $R_1$ | $R_3$ | $R_4$ |
|---|---|---|
| 4-CH$_3$, 2-CH$_3$-pyridin-3-yl-CH$_2$– | H | H |
| 4-CH$_3$, 2-CH$_3$-pyridin-3-yl-CH$_2$– | H | –CH$_3$ |
| 4-CH$_3$, 2-CH$_3$-pyridin-3-yl-CH$_2$– | H | –C$_2$H$_5$ |
| 3-CH$_3$, 5-CH$_3$-pyridin-4-yl-CH$_2$– | H | –OCH$_3$ |
| 3-CH$_3$, 5-CH$_3$-pyridin-4-yl-CH$_2$– | –CH$_3$ | –CH$_3$ |
| 3-CH$_3$, 5-CH$_3$-pyridin-4-yl-CH$_2$– | –CH$_3$ | –C$_2$H$_5$ |
| pyridin-2-yl-CH$_2$– | H | H |
| pyridin-2-yl-CH$_2$– | H | –CH$_3$ |

TABLE II-a-continued $$R_1-N\begin{matrix}CH=N\\ \diagdown\quad\diagup\\ C-N\\ \|\\ O\end{matrix}\begin{matrix}R_3\\ \diagdown\\ N\\ \diagup\\ R_4\end{matrix}$$

| $R_1$ | $R_3$ | $R_4$ |
|---|---|---|
| pyridin-2-ylmethyl (2-pyridyl-CH$_2$–) | H | –C$_2$H$_5$ |

TABLE III 1-(2-pyridylmethyl)-3-methylamidinothiourea
1-(2-pyridylmethyl)-3-ethylamidinothiourea
1-(2-pyridylmethyl)-3-propylamidinothiourea
1-(2-pyridylmethyl)-3-i-propylamidinothiourea
1-(2-pyridylmethyl)-3-butylamidinothiourea
1-(2-pyridylmethyl)-3-i-butylamidinothiourea
1-(2-pyridylmethyl)-3-pentylamidinothiourea
1-(2-pyridylmethyl)-3-propargylamidinothiourea
1-(2-pyridylmethyl)-3-allylamidinothiourea
1-(2-pyridylmethyl)-3-methoxyethylamidinothiourea
1-(2-pyridylmethyl)-3-benzyloxyethylamidinothiourea
1-(2-pyridylmethyl)-3-phenethoxyethylamidinothiourea
1-(2-pyridylmethyl)-3-(N,N—dimethylamidino) thiourea
1-(2-pyridylmethyl)-3-(N,N—diethylamidino) thiourea
1-(2-pyridylmethyl)-3-(N,N—tetramethyleneamidino) thiourea
1-(2-pyridylmethyl)-3-(N,N—pentamethyleneamidino) thiourea
1-(2-pyridylmethyl)-3-(N,N—hexamethyleneamidino) thiourea
1-(3-methyl-2-pyridylmethyl)-3-methylamidinothiourea
1-(3-methyl-2-pyridylmethyl)-3-ethylamidinothiourea
1-(3-methyl-2-pyridylmethyl)-3-propylamidinothiourea
1-(3-methyl-2-pyridylmethyl)-3-i-propylamidinothiourea
1-(3-methyl-2-pyridylmethyl)-3-i-butylamidinothiourea
1-(3-methyl-2-pyridylmethyl)-3-pentylamidinothiourea
1-(3-methyl-2-pyridylmethyl)-3-allylamidinothiourea
1-(3-methyl-2-pyridylmethyl)-3-propargylamidinothiourea
1-(3-methyl-2-pyridylmethyl)-3-cyclopropylamidinothiourea
1-(3-methyl-2-pyridylmethyl)-3-methoxyethylamidinothiourea
1-(3-methyl-2-pyridylmethyl)-3-benzyloxyethylamidinothiourea
1-(3-methyl-2-pyridylmethyl)-3-phenethoxyethylamidinothiourea
1-(3-methyl-2-pyridylmethyl)-3-benzylamidinothiourea
1-(3-methyl-2-pyridylmethyl)-3-(N,N—dimethylamidino) thiourea
1-(3-methyl-2-pyridylmethyl)-3-(N,N—diethylamidino) thiourea
1-(3-methyl-2-pyridylmethyl)-3-(N,N—tetramethyleneamidino) thiourea
1-(3-methyl-2-pyridylmethyl)-3-(N,N—pentamethyleneamidino) thiourea
1-(3-chloro-2-pyridylmethyl)-3-methylamidinothiourea
1-(3-chloro-2-pyridylmethyl)-3-ethylamidinothiourea
1-(3-chloro-2-pyridylmethyl)-3-propylamidinothiourea
1-(3-chloro-2-pyridylmethyl)-3-i-propylamidinothiourea
1-(3-chloro-2-pyridylmethyl)-3-butylamidinothiourea
1-(3-chloro-2-pyridylmethyl)-3-i-butylamidinothiourea
1-(3-chloro-2-pyridylmethyl)-3-t-butylamidinothiourea
1-(3-chloro-2-pyridylmethyl)-3-pentylamidinothiourea
1-(3-chloro-2-pyridylmethyl)-3-allylamidinothiourea
1-(3-chloro-2-pyridylmethyl)-3-propargylamidinothiourea
1-(3-chloro-2-pyridylmethyl)-3-cyclopropylamidinothiourea
1-(3-chloro-2-pyridylmethyl)-3-cyclobutylamidinothiourea
1-(3-chloro-2-pyridylmethyl)-3-(N—[3-cyclopentenyl]amidino) thiourea
1-(3-chloro-2-pyridylmethyl)-3-cyclopropylmethylamidinothiourea
1-(3-chloro-2-pyridylmethyl)-3-methoxyethylamidinothiourea
1-(3-chloro-2-pyridylmethyl)-3-benzyloxyethylamidinothiourea
1-(3-chloro-2-pyridylmethyl)-3-phenethoxyethylamidinothiourea
1-(3-chloro-2-pyridylmethyl)-3-benzylamidinothiourea
1-(3-chloro-2-pyridylmethyl)-3-(N,N—dimethylamidino) thiourea
1-(3-chloro-2-pyridylmethyl)-3-(N,N—diethylamidino) thiourea
1-(3-chloro-2-pyridylmethyl)-3-(N,N—tetramethyleneamidino) thiourea
1-(2-pyridylmethyl)-3-(N,N[3-methyl-3-azapentamethylene]-amidino) thiourea
1-(2-pyridylmethyl)-3-(N,N[3-oxapentamethylene]amidino) thiourea
1-(2-pyridylmethyl)-3-methylamidinothiourea

TABLE III-continued 1-(2-pyridylmethyl)-3-ethylamidinothiourea
1-(2-pyridylmethyl)-3-propylamidinothiourea
1-(2-pyridylmethyl)-3-i-propylamidinothiourea
1-(2-pyridylmethyl)-3-butylamidinothiourea
1-(2-pyridylmethyl)-3-i-butylamidinothiourea
1-(3-pyridylmethyl)-3-t-butylamidinothiourea
1-(3-pyridylmethyl)-3-pentylamidinothiourea
1-(3-pyridylmethyl)-3-allylamidinothiourea
1-(3-pyridylmethyl)-3-propargylamidinothiourea
1-(3-pyridylmethyl)-3-cyclobutylamidinothiourea
1-(3-pyridylmethyl)-3-cyclohexylamidinothiourea
1-(3-pyridylmethyl)-3-benzylamidinothiourea
1-(3-pyridylmethyl)-3-methoxyethylamidinothiourea
1-(3-pyridylmethyl)-3-benzyloxyethylamidinothiourea
1-(3-pyridylmethyl)-3-methoxyethylamidinothiourea
1-(3-pyridylmethyl)-3-benzyloxyethylamidinothiourea
1-(3-pyridylmethyl)-3-phenethoxyethylamidinothiourea
1-(3-pyridylmethyl)-3-(N,N—dimethylamidino) thiourea
1-(3-pyridylmethyl)-3-(N,N—diethylamidino) thiourea
1-(3-pyridylmethyl)-3-(N,N—pentamethyleneamidino) thiourea
1-(4-pyridylmethyl)-3-methylamidinothiourea
1-(4-pyridylmethyl)-3-ethylamidinothiourea
1-(4-pyridylmethyl)-3-propylamidinothiourea
1-(4-pyridylmethyl)-3-i-propylamidinothiourea
1-(4-pyridylmethyl)-3-butylamidinothiourea
1-(4-pyridylmethyl)-3-t-butylamidinothiourea
1-(4-pyridylmethyl)-3-pentylamidinothiourea
1-(4-pyridylmethyl)-3-hexylamidinothiourea
1-(4-pyridylmethyl)-3-propargylamidinothiourea
1-(4-pyridylmethyl)-3-allylamidinothiourea
1-(4-pyridylmethyl)-3-methoxyethylamidinothiourea
1-(4-pyridylmethyl)-3-benzyloxyethylamidinothiourea
1-(4-pyridylmethyl)-3-phenethoxyethylamidinothiourea
1-(4-pyridylmethyl)-3-(N,N—dimethylamidino) thiourea
1-(4-pyridylmethyl)-3-(N,N—diethylamidino) thiourea
1-(4-pyridylmethyl)-3-(N—methyl-N—ethylamidino) thiourea
1-[2-(2-pyridyl)ethyl]-3-methylamidinothiourea
1-[2-(2-pyridyl)ethyl]-3-ethylamidinothiourea
1-[2-(2-pyridyl)ethyl]-3-propylamidinothiourea
1-[2-(2-pyridyl)ethyl]-3-i-propylamidinothiourea
1-[2-(2-pyridyl)ethyl]-3-butylamidinothiourea
1-[2-(2-pyridyl)ethyl]-3-i-butylamidinothiourea
1-[2-(2-pyridyl)ethyl]-3-pentylamidinothiourea
1-[2-(2-pyridyl)ethyl]-3-propargylamidinothiourea
1-[2-(2-pyridyl)ethyl]-3-allylamidinothiourea
1-[2-(2-pyridyl)ethyl]-3-methoxyethylamidinothiourea
1-[2-(2-pyridyl)ethyl]-3-benzyloxyethylamidinothiourea
1-[2-(2-pyridyl)ethyl]-3-phenethoxyethylamidinothiourea
1-[2-(2-pyridyl)ethyl]-3-(N,N—dimethylamidino) thiourea
1-[2-(2-pyridyl)ethyl]-3-(N,N—diethylamidino) thiourea
1-[2-(2-pyridyl)ethyl]-3-(N,N—tetramethyleneamidino) thiourea
1-[2-(2-pyridyl)ethyl]-3-(N,N—pentamethyleneamidino) thiourea
1-[2-(2-pyridyl)ethyl]-3-(N,N—hexamethyleneamidino) thiourea
1-[2-(3-methyl-2-pyridyl)ethyl]-3-methylamidinothiourea
1-[2-(3-methyl-2-pyridyl)ethyl]-3-ethylamidinothiourea
1-[2-(3-methyl-2-pyridyl)ethyl]-3-propylamidinothiourea
1-[2-(3-methyl-2-pyridyl)ethyl]-3-i-propylamidinothiourea
1-[2-(3-methyl-2-pyridyl)ethyl]-3-i-butylamidinothiourea
1-[2-(3-methyl-2-pyridyl)ethyl]-3-pentylamidinothiourea
1-[2-(3-methyl-2-pyridyl)ethyl]-3-allylamidinothiourea
1-[2-(3-methyl-2-pyridyl)ethyl]-3-propargylamidinothiourea
1-[2-(3-methyl-2-pyridyl)ethyl]-3-cyclopropylamidinothiourea
1-[2-(3-methyl-2-pyridyl)ethyl]-3-methoxyethylamidinothiourea
1-[2-(3-methyl-2-pyridyl)ethyl]-3-benzyloxyethylamidinothiourea
1-[2-(3-methyl-2-pyridyl)ethyl]-3-phenethoxyethylamidinothiourea
1-[2-(3-methyl-2-pyridyl)ethyl]-3-benzylamidinothiourea
1-[2-(3-methyl-2-pyridyl)ethyl]-3-(N,N—dimethylamidino) thiourea
1-[2-(3-methyl-2-pyridyl)ethyl]-3-(N,N—diethylamidino) thiourea
1-[2-(3-methyl-2-pyridyl)ethyl]-3-(N,N—tetramethyleneamidino) thiourea
1-[2-(3-methyl-2-pyridyl)ethyl]-3-(N,N—pentamethyleneamidino) thiourea
1-[2-(3-chloro-2-pyridyl)ethyl]-3-methylamidinothiourea
1-[2-(3-chloro-2-pyridyl)ethyl]-3-ethylamidinothiourea
1-[2-(3-chloro-2-pyridyl)ethyl]-3-propylamidinothiourea
1-[2-(3-chloro-2-pyridyl)ethyl]-3-i-propylamidinothiourea
1-[2-(3-chloro-2-pyridyl)ethyl]-3-butylamidinothiourea
1-[2-(3-chloro-2-pyridyl)ethyl]-3-i-butylamidinothiourea
1-[2-(3-chloro-2-pyridyl)ethyl]-3-t-butylamidinothiourea
1-[2-(3-chloro-2-pyridyl)ethyl]-3-pentylamidinothiourea
1-[2-(3-chloro-2-pyridyl)ethyl]-3-allylamidinothiourea
1-[2-(3-chloro-2-pyridyl)ethyl]-3-propargylamidinothiourea

TABLE III-continued

1-[2-(3-chloro-2-pyridyl)ethyl]-3-cyclopropylamidinothiourea
1-[2-(3-chloro-2-pyridyl)ethyl]-3-cyclobutylamidinothiourea
1-[2-(3-chloro-2-pyridyl)ethyl]-3-(N—[3-cyclopentenyl]amidino)thiourea
1-[2-(3-chloro-2-pyridyl)ethyl]-3-cyclopropylmethylamidinothiourea
1-[2-(3-chloro-2-pyridyl)ethyl]-3-methoxyethylamidinothiourea
1-[2-(3-chloro-2-pyridyl)ethyl]-3-benzyloxyethylamidinothiourea
1-[2-(3-chloro-2-pyridyl)ethyl]-3-phenethoxyethylamidinothiourea
1-[2-(3-chloro-2-pyridyl)ethyl]-3-benzylamidinothiourea
1-[2-(3-chloro-2-pyridyl)ethyl]-3-(N,N—dimethylamidino) thiourea
1-[2-(3-chloro-2-pyridyl)ethyl]-3-(N,N—diethylamidino) thiourea
1-[2-(3-chloro-2-pyridyl)ethyl]-3-(N,N—tetramethyleneamidino) thiourea
1-[2-(2-pyridyl)ethyl]-3-(N,N[3-methyl-3-azapentamethylene]-amidino) thiourea
1-[2-(2-pyridyl)ethyl]-3-(N,N[3-oxapentamethylene]amidino) thiourea
1-[2-(2-pyridyl)ethyl]-3-methylamidinothiourea
1-[2-(2-pyridyl)ethyl]-3-ethylamidinothiourea
1-[2-(2-pyridyl)ethyl]-3-propylamidinothiourea
1-[2-(2-pyridyl)ethyl]-3-i-propylamidinothiourea
1-[2-(2-pyridyl)ethyl]-3-butylamidinothiourea
1-[2-(2-pyridyl)ethyl]-3-i-butylamidinothiourea
1-[2-(2-pyridyl)ethyl]-3-t-butylamidinothiourea
1-[2-(3-pyridyl)ethyl]-3-pentylamidinothiourea
1-[2-(3-pyridyl)ethyl]-3-allylamidinothiourea
1-[2-(3-pyridyl)ethyl]-3-propargylamidinothiourea
1-[2-(3-pyridyl)ethyl]-3-cyclobutylamidinothiourea
1-[2-(3-pyridyl)ethyl]-3-cyclohexylamidinothiourea
1-[2-(3-pyridyl)ethyl]-3-benzylamidinothiourea
1-[2-(3-pyridyl)ethyl]-3-methoxyethylamidinothiourea
1-[2-(3-pyridyl)ethyl]-3-benzyloxyethylamidinothiourea
1-[2-(3-pyridyl)ethyl]-3-methoxyethylamidinothiourea
1-[2-(3-pyridyl)ethyl]-3-benzyloxyethylamidinothiourea
1-[2-(3-pyridyl)ethyl]-3-phenethoxyethylamidinothiourea
1-[2-(3-pyridyl)ethyl]-3-(N,N—dimethylamidino) thiourea
1-[2-(3-pyridyl)ethyl]-3-(N,N—diethylamidino) thiourea
1[8 2-(3-pyridyl)ethyl]-3-(N,N—pentamethyleneamidino) thiourea
1-[2-(4-pyridyl)ethyl]-3-methylamidinothiourea
1-[2-(4-pyridyl)ethyl]-3-ethylamidinothiourea
1-[2-(4-pyridyl)ethyl]-3-propylamidinothiourea
1-[2-(4-pyridyl)ethyl]-3-i-propylamidinothiourea
1-[2-(4-pyridyl)ethyl]-3-butylamidinothiourea
1-[2-(4-pyridyl)ethyl]-3-t-butylamidinothiourea
1-[2-(4-pyridyl)ethyl]-3-pentylamidinothiourea
1-[2-(4-pyridyl)ethyl]-3-hexylamidinothiourea
1-[2-(4-pyridyl)ethyl]-3-propargylamidinothiourea
1-[2-(4-pyridyl)ethyl]-3-allylamidinothiourea
1-[2-(4-pyridyl)ethyl]-3-methoxyethylamidinothiourea
1-[2-(4-pyridyl)ethyl]-3-benzyloxyethylamidinothiourea
1-[2-(4-pyridyl)ethyl]-3-phenethoxyethylamidinothiourea
1-[2-(4-pyridyl)ethyl]-3-(N,N—dimethylamidino) thiourea
1-[2-(4-pyridyl)ethyl]-3-(N,N—diethylamidino) thiourea
1-[2-(4-pyridyl)ethyl]-3-(N—methyl-N—ethylamidino) thiourea
1-[3-(2-pyridyl)propyl]-3-methylamidinothiourea
1-[3-(2-pyridyl)propyl]-3-ethylamidinothiourea
1-[3-(2-pyridyl)propyl]-3-propylamidinothiourea
1-[3-(2-pyridyl)propyl]-3-i-propylamidinothiourea
1-[3-(2-pyridyl)propyl]-3-butylamidinothiourea
1-[3-(2-pyridyl)propyl]-3-i-butylamidinothiourea
1-[3-(2-pyridyl)propyl]-3-pentylamidinothiourea
1-[3-(2-pyridyl)propyl]-3-propargylamidinothiourea
1-[3-(2-pyridyl)propyl]-3-allylamidinothiourea
1-[3-(2-pyridyl)propyl]-3-methoxyethylamidinothiourea
1-[3-(2-pyridyl)propyl]-3-benzyloxyethylamidinothiourea
1-[3-(2-pyridyl)propyl]-3-phenethoxyethylamidinothiourea
1-[3-(2-pyridyl)propyl]-3-(N,N—dimethylamidino) thiourea
1-[3-(2-pyridyl)propyl]-3-(N,N—diethylamidino) thiourea
1-[3-(2-pyridyl)propyl]-3-(N,N—tetramethyleneamidino) thiourea
1-[3-(2-pyridyl)propyl]-3-(N,N—pentamethyleneamidino) thiourea
1-[3-(2-pyridyl)propyl]-3-(N,N—hexamethyleneamidino) thiourea
1-[3-(3-methyl-2-pyridyl)propyl]-3-methylamidinothiourea
1-[3-(3-methyl-2-pyridyl)propyl]-3-ethylamidinothiourea
1-[3-(3-methyl-2-pyridyl)propyl]-3-propylamidinothiourea
1-[3-(3-methyl-2-pyridyl)propyl]-3-i-propylamidinothiourea
1-[3-(3-methyl-2-pyridyl)propyl]-3-i-butylamidinothiourea
1-[3-(3-methyl-2-pyridyl)propyl]-3-pentylamidinothiourea
1-[3-(3-methyl-2-pyridyl)propyl]-3-allylamidinothiourea
1-[3-(3-methyl-2-pyridyl)propyl]-3-propargylamidinothiourea
1-[3-(3-methyl-2-pyridyl)propyl]-3-cyclopropylamidinothiourea
1-[3-(3-methyl-2-pyridyl)propyl]-3-methoxyethylamidinothiourea
1-[3-(3-methyl-2-pyridyl)propyl]-3-benzyloxyethylamidinothiourea
1-[3-(3-methyl-2-pyridyl)propyl]-3-phenethoxyethylamidinothiourea
1-[3-(3-methyl-2-pyridyl)propyl]-3-benzylamidinothiourea
1-[3-(3-methyl-2-pridyl)propyl]-3-(N,N—dimethylamidino) thiourea
1-[3-(3-methyl-2-pridyl)propyl]-3-(N,N—diethylamidino) thiourea
1-[3-(3-methyl-2-pyridyl)propyl]-3-(N,N—tetramethyleneamidino) thiourea
1-[3-(3-methyl-2-pyridyl)propyl]-3-(N,N—pentamethyleneamidino) thiourea
1-[3-(3-chloro-2-pyridyl)propyl]-3-methylamidinothiourea
1-[3-(3-chloro-2-pyridyl)propyl]-3-ethylamidinothiourea
1-[3-(3-chloro-2-pyridyl)propyl]-3-propylamidinothiourea
1-[3-(3-chloro-2-pyridyl)propyl]-3-i-propylamidinothiourea
1-[3-(3-chloro-2-pyridyl)propyl]-3-butylamidinothiourea
1-[3-(3-chloro-2-pyridyl)propyl]-3-i-butylamidinothiourea
1-[3-(3-chloro-2-pyridyl)propyl]-3-t-butylamidinothiourea
1-[3-(3-chloro-2-pyridyl)propyl]-3-pentylamidinothiourea
1-[3-(3-chloro-2-pyridyl)propyl]-3-allylamidinothiourea
1-[3-(3-chloro-2-pyridyl)propyl]-3-propargylamidinothiourea
1-[3-(3-chloro-2-pyridyl)propyl]-3-cyclopropylamidinothiourea
1-[3-(3-chloro-2-pyridyl)propyl]-3-cyclobutylamidinothiourea
1-[3-(3-chloro-2-pyridyl)propyl]-3-(N—[3-cyclopentenyl] amidino) thiourea
1-[3-(3-chloro-2-pyridyl)propyl]-3-cyclopropylmethylamidinothiourea
1-[3-(3-chloro-2-pyridyl)propyl]-3-methoxyethylamidinothiourea
1-[3-(3-chloro-2-pyridyl)propyl]-3-benzyloxyethylamidinothiourea
1-[3-(3-chloro-2-pyridyl)propyl]-3-phenethoxyethylamidinothiourea
1-[3-(3-chloro-2-pyridyl)propyl]-3-benzylamidinothiourea
1-[3-(3-chloro-2-pyridyl)propyl]-3-(N,N—dimethylamidino) thiourea
1-[3-(3-chloro-2-pyridyl)propyl]-3-(N,N—diethylamidino)thiourea
1-[3-(3-chloro-2-pyridyl)propyl]-3-(N,N—tetramethyleneamidino) thiourea
1-[3-(2-pyridyl)propyl]-3-(N,N[3-methyl-3-azapentamethylene]-amidino) thiourea
1-[3-(2-pyridyl)propyl]-3-(N,N[3-oxapentamethylene]amidino) thiourea
1-[3-(2-pyridyl)propyl]-3-methylamidinothiourea
1-[3-(2-pyridyl)propyl]-3-ethylamidinothiourea
1-[3-(2-pyridyl)propyl]-3-propylamidinothiourea
1-[3-(2-pyridyl)propyl]-3-i-propylamidinothiourea
1-[3-(2-pyridyl)propyl]-3-butylamidinothiourea
1-[3-(2-pyridyl)propyl]-3-i-butylamidinothiourea
1-[3-(2-pyridyl)propyl]-3-t-butylamidinothiourea
1-[3-(3-pyridyl)propyl]-3-pentylamidinothiourea
1-[3-(3-pyridyl)propyl]-3-allylamidinothiourea
1-[3-(3-pyridyl)propyl]-3-propargylamidinothiourea
1-[3-(3-pyridyl)propyl]-3-cyclobutylamidinothiourea
1-[3-(3-pyridyl)propyl]-3-cyclohexylamidinothiourea
1-[3-(3-pyridyl)propyl]-3-benzylamidinothiourea
1-[3-(3-pyridyl)propyl]-3-methoxyethylamidinothiourea
1-[3-(3-pyridyl)propyl]-3-benzyloxyethylamidinothiourea
1-[3-(3-pyridyl)propyl]-3-methoxyethylamidinothiourea
1-[3-(3-pyridyl)propyl]-3-benzyloxyethylamidinothiourea
1-[3-(3-pyridyl)propyl]-3-phenethoxyethylamidinothiourea
1-[3-(3-pyridyl)propyl]-3-(N,N—dimethylamidino) thiourea
1-[3-(3-pyridyl)propyl]-3-(N,N—diethylamidino) thiourea
1-[3-(3-pyridyl)propyl]-3-(N,N—pentamethyleneamidino) thiourea
1-[3-(4-pyridyl)propyl]-3-methylamidinothiourea
1-[3-(4-pyridyl)propyl]-3-ethylamidinothiourea
1-[3-(4-pyridyl)propyl]-3-propylamidinothiourea
1-[3-(4-pyridyl)propyl]-3-i-propylamidinothiourea
1-[3-(4-pyridyl)propyl]-3-butylamidinothiourea
1-[3-(4-pyridyl)propyl]-3-t-butylamidinothiourea
1-[3-(4-pyridyl)propyl]-3-pentylamidinothiourea
1-[3-(4-pyridyl)propyl]-3-hexylamidinothiourea
1-[3-(4-pyridyl)propyl]-3-propargylamidinothiourea
1-[3-(4-pyridyl)propyl]-3-allylamidinothiourea
1-[3-(4-pyridyl)propyl]-3-methoxyethylamidinothiourea
1-[3-(4-pyridyl)propyl]-3-benzyloxyethylamidinothiourea
1-[3-(4-pyridyl)propyl]-3-phenethoxyethylamidinothiourea
1-[3-(4-pyridyl)propyl]-3-(N,N—dimethylamidino) thiourea
1-[3-)4-pyridyl)propyl]-3-(N,N—diethylamidino) thiourea
1-[3-(4-pyridyl)propyl]-3-(N—methyl-N—ethylamidino) thiourea

TABLE IV 1-(2-pyridylmethyl)-4-methylamino-1,2-dihydro-1,3,5-triazin-2-thione
1-(2-pyridylmethyl)-4-ethylamino-1,2-dihydro-1,3,5-triazin-2-thione

TABLE IV-continued 1-(2-pyridylmethyl)-4-propylamino-1,2-dihydro-1,3,5-triazin-2-thione
1-(2-pyridylmethyl)-4-i-propylamino-1,2-dihydro-1,3,5-triazin-2-thione
1-(2-pyridylmethyl)-4-butylamino-1,2-dihydro-1,3,5-triazin-2-thione
1-(2-pyridylmethyl)-4-t-butylamino-1,2-dihydro-1,3,5-triazin-2-thione
1-(2-pyridylmethyl)-4-pentylamino-1,2-dihydro-1,3,5-triazin-2-thione
1-(2-pyridylmethyl)-4-allylamino-1,2-dihydro-1,3,5-triazin-2-thione
1-(2-pyridylmethyl)-4-propargylamino-1,2-dihydro-1,3,5,-triazin-2-thione
1-(2-pyridylmethyl)-4-cyclopropylamino-1,2-dihydro-1,3,5-triazin-2-thione
1-(2-pyridylmethyl)-4-methoxyethylamino-1,2-dihydro-1,3,5-triazin-2-thione
1-(2-pyridylmethyl)-4-benzyloxyethylamino-1,2-dihydro-1,3,5-triazin-2-thione
1-(2-pyridylmethyl)-4-phenethoxyethylamino-1,2-dihydro-1,3,5-triazin-2-thione
1-(2-pyridylmethyl)-4-benzylamino-1,2-dihydro-1,3,5-triazin-2-thione
1-(2-pyridylmethyl)-4-(N,N—dimethylamino)-1,2-dihydro-1,3,5-triazin-2-thione
1-(2-pyridylmethyl)-4-(N,N—diethylamino)-1,2-dihydro-1,3,5-triazin-2-thione
1-(2-pyridylmethyl)-4-(N—pyrrolidinyl)-1,2-dihydro-1,3,5-triazin-2-thione
1-(2-pyridylmethyl)-4-(N—piperidyl)-1,2-hydro-1,3,5-triazin-2-thione
1-(3-methyl-2-pyridylmethyl)-4-methylamino-1,2-dihydro-1,3,5-triazin-2-thione
1-(3-methyl-2-pyridylmethyl)-4-ethylamino-1,2-dihydro-1,3,5-triazin-2-thione
1-(3-methyl-2-pyridylmethyl)-4-propylamino-1,2-hydro-1,3,5-triazin-2-thione
1-(3-methyl-2-pyridylmethyl)-4-i-propylamino-1,2-dihydro-1,3,5-triazin-2-thione
1-(3-methyl-2-pyridylmethyl)-4-butylamino-1,2-dihydro-1,3,5-triazin-2-thione
1-(2-morpholinylmethyl)-4-methylamino-1,2-dihydro-1,3,5-triazin-2-thione
1-(2-pyrimidinylmethyl)-4-methylamino-1,2-dihydro-1,3,5-triazin-2-thione
1-(4-pyrimidinylmethyl)-4-methylamino-1,2-dihydro-1,3,5-triazin-2-thione
1-(2-quinolinylmethyl)-4-methylamino-1,2-dihydro-1,3,5-triazin-2-thione
1-(4-quinolinylmethyl)-4-methylamino-1,2-dihydro-1,3,5-triazin-2-thione
1-(1-isoquinolinylmethyl)-4-methylamino-1,2-dihydro-1,3,5-triazin-2-thione
1-(2-dihydroindolinylmethyl)-4-methylamino-1,2-dihydro-1,3,5-triazin-2-thione
1-furfuryl-4-ethylamino-1,2-dihydro-1,3,5-triazin-2-thione
1-furfuryl-4-propylamino-1,2-dihydro-1,3,5-triazin-2-thione
1-furfuryl-4-i-propylamino-1,2-dihydro-1,3,5-triazin-2-thione
1-furfuryl-4-butylamino-1,2-dihydro-1,3,5-triazin-2-thione
1-furfuryl-4-(i-butylamino)-1,2-dihydro-1,3,5-triazin-2-thione
1-(2-pyridylmethyl)-4-(sec-butylamino)-1,2-dihydro-1,3,5-triazin-2-thione
1-(2-pyridylmethyl)-4-(t-butylamino)-1,2-dihydro-1,3,5-triazin-2-thione
1-(2-pyridylmethyl)-4-pentylamino-1,2-dihydro-1,3,5-triazin-2-thione
1-(2-pyridylmethyl)-4-hexylamino-1,2-dihydro-1,3,5-triazin-2-thione
1-(2-pyridylmethyl)-4-heptylamino-1,2-dihydro-1,3,5-triazin-2-thione
1-(2-pyridylmethyl)-4-cyclopropylamino-1,2-dihydro-1,3,5-triazin-2-thione
1-(2-pyridylmethyl)-4-cyclobutylamino-1,2-dihydro-1,3,5-triazin-2-thione
1-(2-pyridylmethyl)-4-cyclopentylamino-1,2-dihydro-1,3,5-triazin-2-thione
1-(2-pyridylmethyl)-4-cyclohexylamino-1,2-dihydro-1,3,5-triazin-2-thione
1-(2-pyridylmethyl)-4-anilino-1,2-dihydro-1,3,5-triazin-2-thione
1-(2-pyridylmethyl)-4-benzylamino-1,2-dihydro-1,3,5-triazin-2-thione
1-(2-pyridylmethyl)-4-phenethylamino-1,2-dihydro-1,3,5-triazin-2-thione
1-(2-pyridylmethyl)-4-(N—methyl-N—benzylamino)-1,2-dihydro-1,3,5-triazin-2-thione
1-(2-pyridylmethyl)-4-(N,N—dibenzylamino)-1,2-dihydro-1,3,5-triazin-2-thione
1-(3-methyl-tetrahydrofurfuryl)-4-amino-1,2-dihydro-1,3,5-triazin-2-thione
1-tetrahydrofurfuryl-4-amino-1,2-dihydro-1,3,5-triazin-2-thione
1-(2-methyl-tetrahydrofurfuryl)-4-amino-1,2-dihydro-1,3,5-triazin-2-thione
1-(2-methyl-3-pyridylmethyl)-4-methylamino-1,2-dihydro-1,3,5-triazin-2-thione
1-(2-ethyl-3-pyridylmethyl)-4-methylamino-1,2-hydro-1,3,5-triazin-2-thione
1-(2,6'-dimethyl-3-pyridylmethyl)-4-methylamino-1,2-hydro-1,3,5-triazin-2-thione
1-(2-ethyl-6-bromo-3-pyridylmethyl)-4-methylamino-1,2-dihydro-1,3,5-triazin-2-thione
1-(2-ethyl-6-fluoro-3-pyridylmethyl)-4-methylamino-1,2-dihydro-1,3,5-triazin-2-thione
1-(3-cyano-2-thiophenylmethyl)-4-methylamino-1,2-dihydro-1,3,5-triazin-2-thione
1-(3-carbomethoxy-2-thiophenylmethyl)-4-methylamino-1,2-dihydro-1,3,5-triazin-2-thione
1-(3-carboethoxy-2-thiophenylmethyl)-4-methylamino-1,2-dihydro-1,3,5-triazin-2-thione
1-(2-methoxy-3-pyridylmethyl)-4-(N,N—diethylamino)-1,2-dihydro-1,3,5-triazin-2-thione
1-(2-ethoxy-3-pyridylmethyl)-4-(N—ethyl-N—methylamino)-1,2-dihydro-1,3,5-triazin-2-thione
1-(2-chloro-3-pyridylmethyl)-4-(N—methyl-N—propylamino)-1,2-dihydro-1,3,5-triazin-2-thione
1-furfuryl-4-(N—methyl-N-butylamino)-1,2-dihydro-1,3,5-triazin-2-thione
1-furfuryl-4-(N,N—dipropylamino)-1,2-dihydro-1,3,5-triazin-2-thione
1-furfuryl-4-(N—ethyl-N—propylamino)-1,2-dihydro-1,3,5-triazin-2-thione
1-furfuryl-4-(N—methyl-N—benzyloxypropylamino)-1,2-dihydro-1,3,5-triazin-2-thione
1-furfuryl-4-(N—methyl-N—phenethoxyethylamino)-1,2-dihydro-1,3,5-triazin-2-thione
1-furfuryl-4-(N—methyl-N—benzyloxyethylamino)-1,2-dihydro-1,3,5-triazin-2-thione
1-furfuryl-4(N—pyrrolidinyl)-1,2-dihydro-1,3,5-triazin-2-thione
1-furfuryl-4-(N—piperidyl)-1,2-dihydro-1,3,5-triazin-2-thione
1-furfuryl-4-(N—azipinyl)-1,2-dihydro-1,3,5-triazin-2-thione
1-furfuryl-4-(N—morpholinyl)-1,2-dihydro-1,3,5-triazin-2-thione
1-furfuryl-4-[3-(N—methyl piperidyl)]-1,2-dihydro-1,3,5-triazin-2-thione
1-(3-chloro-2-pyridylmethyl)-4-propylamino-1,2-dihydro-1,3,5-triazin-2-thione
1-(3-chloro-2-pyridylmethyl)-4-i-propylamino-1,2-dihydro-1,3,5-triazin-2-thione
1-(3-chloro-2-pyridylmethyl)-4-butylamino-1,2-dihydro-1,3,5-triazin-2-thione
1-(3-chloro-2-pyridylmethyl)-4-i-butylamino-1,2-dihydro-1,3,5-triazin-2-thione
1-(3-chloro-2-pyridylmethyl)-4-t-butylamino-1,2-dihydro-1,3,5-triazin-2-thione
1-(3-chloro-2-pyridylmethyl)-4-pentylamino-1,2-dihydro-1,3,5-triazin-2-thione
1-(3-chloro-2-pyridylmethyl)-4-propargylamino-1,2-dihydro-1,3,5-triazin-2-thione
1-(3-chloro-2-pyridylmethyl)-4-cyclobutylamino-1,2-dihydro-1,3,5-triazin-2-thione
1-(3-chloro-2-pyridylmethyl)-4-cyclohexylamino-1,2-dihydro-1,3,5-triazin-2-thione
1-(3-chloro-2-pyridylmethyl)-4-benzylamino-1,2-dihydro-1,3,5-triazin-2-thione
1-(3-chloro-2-pyridylmethyl)-4-methoxyethylamino-1,2-dihydro-1,3,5-triazin-2-thione
1-(3-chloro-2-pyridylmethyl)-4-benzyloxyethylamino-1,2-dihydro-1,3,5-triazin-2-thione
1-(3-chloro-2-pyridylmethyl)-4-phenethoxyethylamino-1,2-dihydro-1,3,5-triazin-2-thione
1-(3-chloro-2-pyridylmethyl)-4-(N,N—diethylamino)-1,2-dihydro-1,3,5-triazin-2-thione
1-(3-chloro-2-pyridylmethyl)-4-(N—piperidinyl)-1,2-dihydro-1,3,5-triazin-2-thione
1-(3-pyridylmethyl)-4-methylamino-1,2-dihydro-1,3,5-triazin-2-thione
1-(3-pyridylmethyl)-4-ethylamino-1,2-dihydro-1,3,5-triazin-2-thione
1-(3-pyridylmethyl)-4-propylamino-1,2-dihydro-1,3,5-triazin-2-thione
1-(3-pyridylmethyl)-4-i-propylamino-1,2-dihydro-1,3,5-triazin-2-thione
1-(3-pyridylmethyl)-4-butylamino-1,2-dihydro-1,3,5-triazin-2-thione
1-(3-pyridylmethyl)-4-t-butylamino-1,2-dihydro-1,3,5-triazin-2-thione
1-(3-pyridylmethyl)-4-pentylamino-1,2-dihydro-1,3,5-triazin-2-thione
1-(3-pyridylmethyl)-4-hexylamino-1,2-dihydro-1,3,5-triazin-2-thione

TABLE V

Structure:
$$R_1-N(-CH=N-)-C(=N-)-N(R_3)(R_4)$$ with =X (X = O, S) on the central carbon

| R₁ | R₃ | R₄ |
|---|---|---|
| 2-pyridyl-CH₂ | H | H |
| 2-pyridyl-CH₂ | H | —CH₃ |
| 2-pyridyl-CH₂ | H | —C₂H₅ |
| 2-pyridyl-CH₂ | —CH₃ | —CH₃ |
| 2-pyridyl-CH₂ | H | —OCH₃ |
| (3-CH₃-2-pyridyl)-CH₂ | H | —CH₃ |
| (3-CH₃-2-pyridyl)-CH₂ | —CH₃ | —CH₃ |
| (3-CH₃-2-pyridyl)-CH₂ | —C₂H₅ | —C₂H₅ |
| (2,4-di-CH₃-3-pyridyl)-CH₂ | H | H |
| (2,4-di-CH₃-3-pyridyl)-CH₂ | H | —CH₃ |
| (2,4-di-CH₃-3-pyridyl)-CH₂ | H | —C₂H₅ |
| (3,5-di-CH₃-4-pyridyl)-CH₂ | H | —OCH₃ |
| (3,5-di-CH₃-4-pyridyl)-CH₂ | —CH₃ | —CH₃ |
| (3,5-di-CH₃-4-pyridyl)-CH₂ | —CH₃ | —C₂H₅ |
| (3-C₂H₅-2-pyridyl)-CH₂ | H | H |
| (3-C₂H₅-2-pyridyl)-CH₂ | H | —CH₃ |
| (3-C₂H₅-2-pyridyl)-CH₂ | H | —C₂H₅ |
| (4,6-di-CH₃-5-pyrimidinyl)-CH₂ | —CH₃ | —CH₃ |

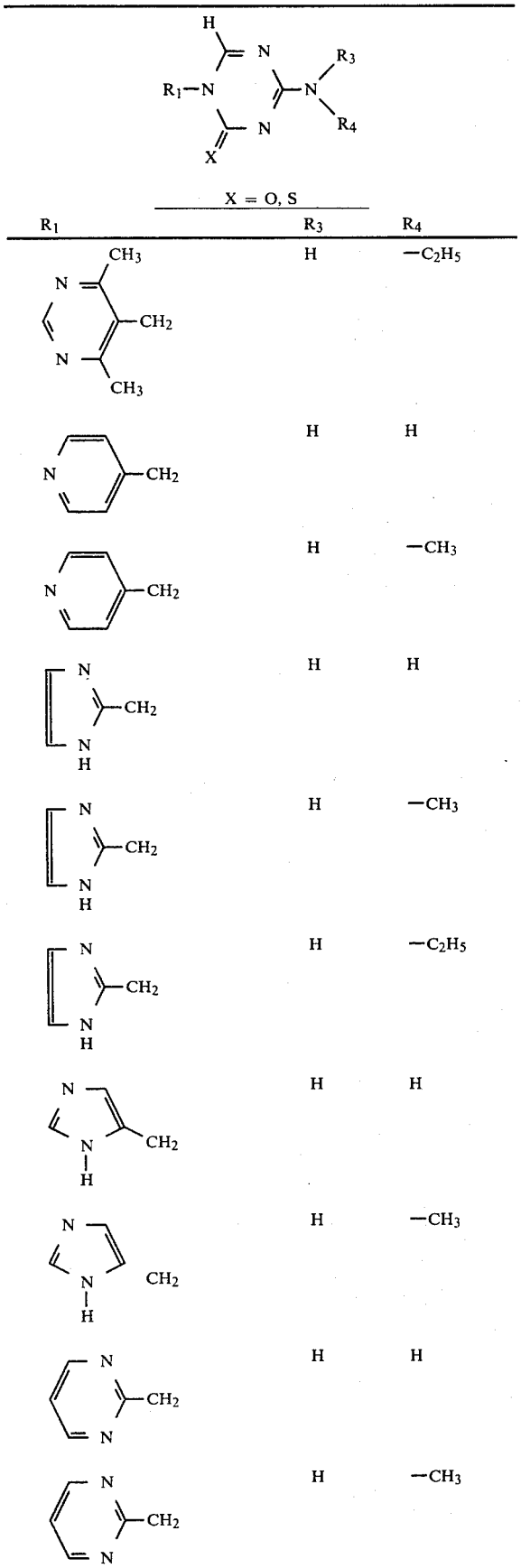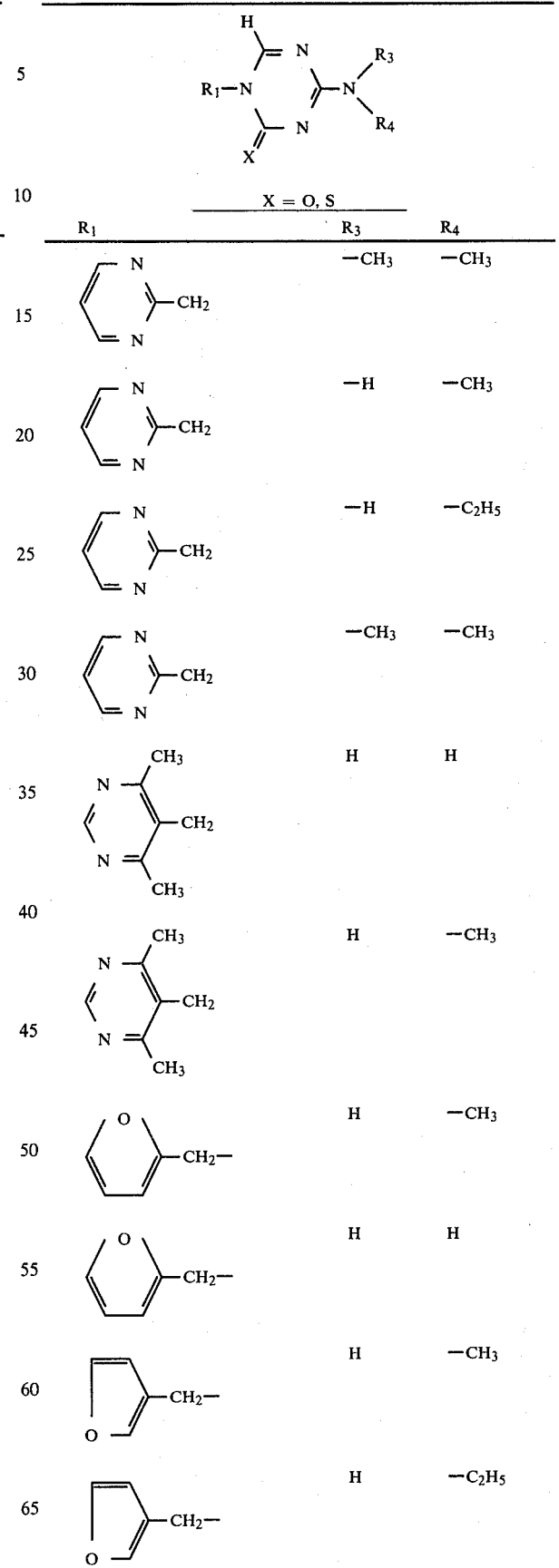

TABLE V-continued
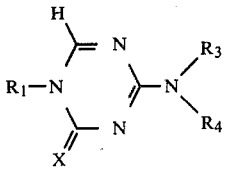
X = O, S
| R₁ | R₃ | R₄ |
|---|---|---|
| 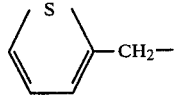 | H | —CH₃ |
| 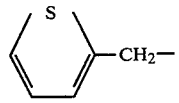 | —CH₃ | —CH₃ |
| 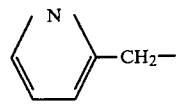 | —H | —CH₃ |
| 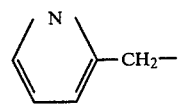 | —H | —C₂H₅ |
| 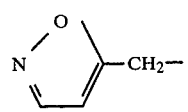 | —H | —CH₃ |
| 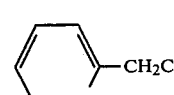 | H | H |
|  | H | —CH₃ |
| 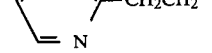 | H | —C₂H₅ |
| 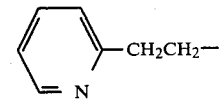 | —CH₃ | —CH₃ |
| 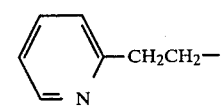 | H | —OCH₃ |
| 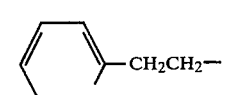 | H | —CH₃ |
| 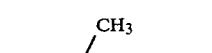 | —CH₃ | —CH₃ |
| 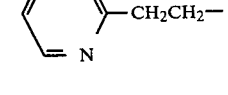 | —C₂H₅ | —C₂H₅ |
| 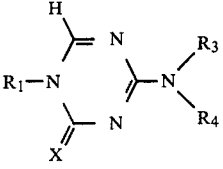 | H | H |
| 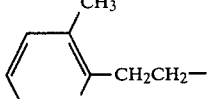 | H | —CH₃ |
| 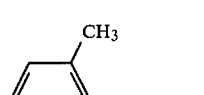 | H | —C₂H₅ |
| 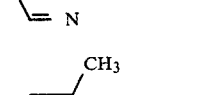 | H | —OCH₃ |
| 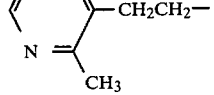 | —CH₃ | —CH₃ |
| 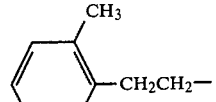 | —CH₃ | —C₂H₅ |

4,387,225

TABLE V-continued

Structure:
```
        H
        |
        C=N      R3
        |      /
   R1—N       N
        \    / \
         C      R4
         ||
         N
         |
         X
```

X = O, S

| R1 | R3 | R4 |
|---|---|---|
| 3-ethyl-2-pyridyl-CH2CH2— | H | H |
| 3-ethyl-2-pyridyl-CH2CH2— | H | —CH3 |
| 3-ethyl-2-pyridyl-CH2CH2— | H | —C2H5 |
| 2-pyrimidinyl-CH2CH2— | H | H |
| 2-pyrimidinyl-CH2CH2— | H | —CH3 |
| 2-pyrimidinyl-CH2CH2— | —CH3 | —CH3 |
| 2-pyrimidinyl-CH2CH2— | —H | —CH3 |
| 2-pyrimidinyl-CH2CH2— | —H | —C2H5 |
| 2-pyrimidinyl-CH2CH2— | —CH3 | —CH3 |
| 4,6-dimethyl-5-pyrimidinyl-CH2CH2— | H | H |
| 4,6-dimethyl-5-pyrimidinyl-CH2CH2— | H | —CH3 |
| 4,6-dimethyl-5-pyrimidinyl-CH2CH2— | —CH3 | —CH3 |
| 4,6-dimethyl-5-pyrimidinyl-CH2CH2— | H | —C2H5 |
| 3-pyridyl-CH2CH2— | H | H |
| 3-pyridyl-CH2CH2— | H | —CH3 |
| 2-imidazolyl-CH2CH2— | H | H |
| 2-imidazolyl-CH2CH2— | H | —CH3 |
| 2-imidazolyl-CH2CH2— | H | —C2H5 |
| 1H-imidazol-4-yl-CH2CH2— | H | H |

TABLE V-continued

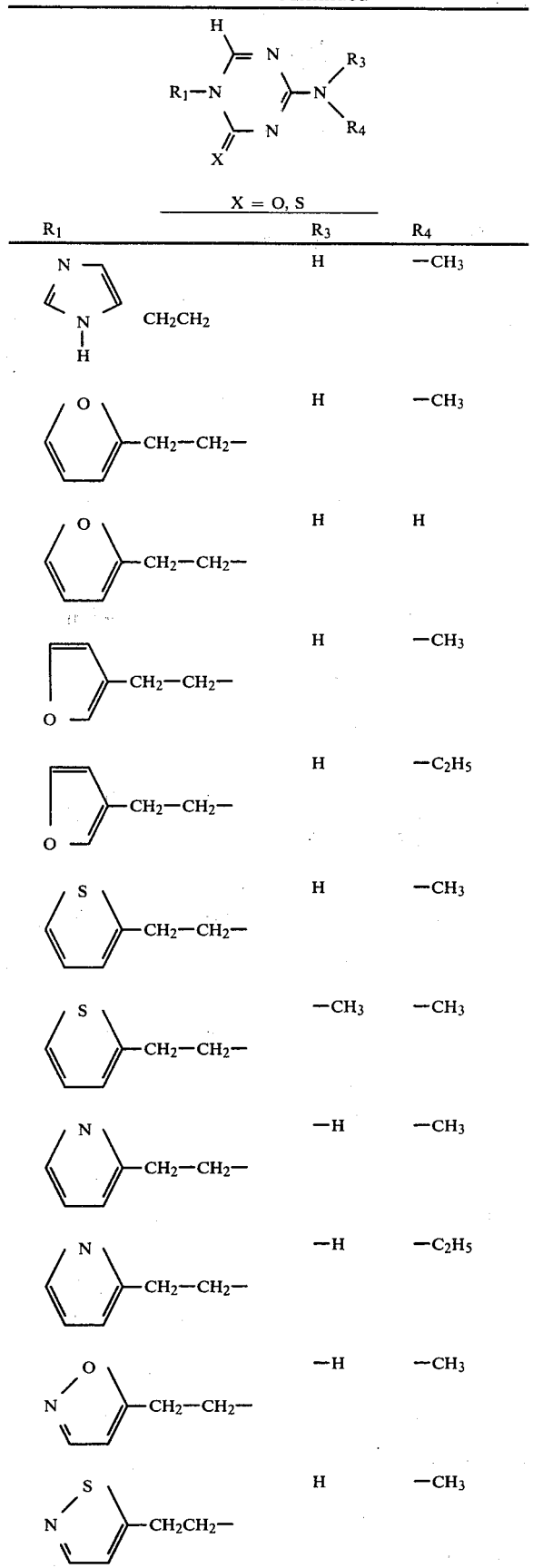
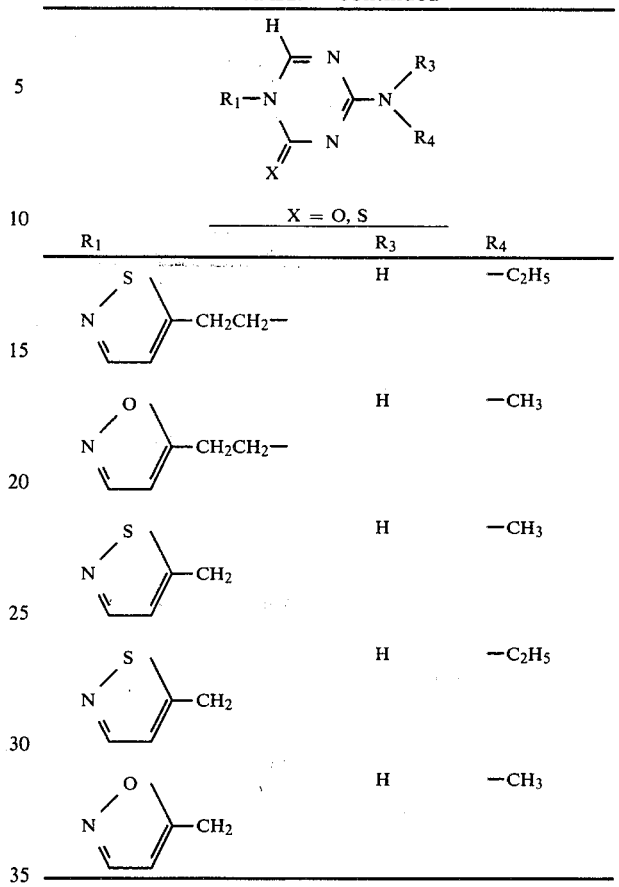

1-aryl-1,2-dihydro-s-triazine derivatives are known to possess a broad spectrum of biological activity (heterocyclic Compounds, Vol. 7, John Wiley & Sons, Inc., 1961, p. 717–18). The novel compounds of this invention constitute a new class of 1-aralkyl-1,2-dihydro-2-triazines, particularly 1-heterocyclic alkylene-1,2-dihydro-1,3,5-triazin-2-ones which similarly have a broad spectrum of biological activity. Thus, these compounds possess useful gastrointestinal actions and can be used for example as antidiarrheal agents for the treatment of gastrointestinal disorders. Whereas amidinoureas also have local anesthetic and other pharmacological effects when administered at dose levels for effective antidiarrheal action, certain of the novel triazinones possess good antidiarrheal activity without local anesthetic or other side effects at active dose levels. Certain of the novel triazine derivatives possess other gastrogenic and related effects, particularly antisecretory action, making them useful in the treatment of such gastrointestinal disorders as peptic ulcers. Compounds of this series also possess anti-motility and spasmolytic effects making them useful in the control of muscle spasm particularly stomach or intestinal spasms. Certain of the compounds also exhibit novel effects on nerve impulse transmissions wherein multiple high frequency nerve transmissions are blocked.

The amidinoureas from which the novel triazine derivatives are prepared according to this invention possess useful pharmacological properties including antidiarrheal activity in mammalian species. Generally, it has been found that the antidiarrheal properties of the amidinourea are not lost in cyclizing to the corresponding triazine derivative. Accordingly, the novel triazine derivatives of this invention are also useful antidiarrheal agents as shown by test results in animals, which, based on previous experience with the corresponding amidinoureas, show good correlation to activity in humans.

Various tests can be carried out in animal models to show the ability of the heterocyclic alkylene triazinones of this invention to exhibit reactions that can be correlated with anti-diarrheal activity in humans. The following tests show the ability of the compounds of this invention to inhibit diarrhea in animals and are known to correlate well with antidiarrheal activity in humans. These are considered to be standard tests used to determine antidiarrheal properties. This correlation can be shown by the activities of compounds known to be clinically active.

The test compound is dissolved in distilled water, unless otherwise stated. The $ED_{50}$ values and 95% confidence limits are calculated according to a method described by D. F. Finney (Probit Analysis, 2nd Ed., University Press, Cambridge, p. 236, 1964).

1. Antagonism of Castor Oil-induced Diarrhea in Mice

A modified test described by Niemegeers et al. (Arzneim-Forscth 22, 516–518, 1972) was used. Groups of ten male Swiss Webster mice (22–25 g) were randomly selected for dosing. Castor oil (Fischer Scientific Co.), 0.3 ml/mouse, was given orally one hour after an oral dose of test compound or the vehicle. After dosing with castor oil, each mouse was placed into an individual wire cage and observed for six hours for diarrhea.

2. Antagonism of Castor Oil-induced Diarrhea in Rats

A test described by Niemegeers et al. (supra) was used. Groups of ten female Wistar rats (180–200 g) were randomly selected for dosing. In addition, groups of ten female Sprague-Dawly rats (180–200 g) were used to determine strain difference. Castor oil (Fisher Scientific Co.), 1 ml/rat, was given orally one hour after an oral dose of test compound or the vehicle. After dosing with castor oil, each rat was placed into an individual wire cage and observed for six hours for diarrhea.

3. Antagonism of Chemically-induced Diarrhea in Mice

Male Swiss Webster mice (18–22 g) in groups of 10–20 mice were randomly selected for oral dosing with test compound or the vehicle one hour before the intraperitoneal injection of either 400 $\mu g/kg$ of Carbachol (carbamycholine chloride, Sigma Chemical Co., St. Louis, Missouri); or, 200 $\mu g/kg$ of serotonin creatinine sulfate (Schwartz/Mann Biochemicals, Orangeburg, New York). After each mouse was injected, it was placed into an individual wire cage and observed for diarrhea.

4. Inhibition of the Gastrointestinal Transit Time of a Charcoal Meal in Mice

A charcoal suspension (10 ml/kg of a 10% suspension) was given orally to groups of ten Swiss Webster male mice (18–22 g) one hour after an oral dose of test compound or vehicle. The mice were sacrificed by cervical dislocation 30 minutes after the charcoal meal and the distance in millimeters that the charcoal meal traveled through the small intestine was measured and compared to the controls.

$$\frac{\text{Mean distance in controls} - \text{mean distance in treated}}{\text{Mean distance in controls}} \times 100 =$$

% Inhibition

5. The Effect of Naloxone on the Inhibitory Actions of Triazinones on Gastrointestinal Motility Male Swiss Webster mice (18–20 g) in groups of ten were randomly selected for dosing with test compound or the vehicle alone and concomitantly with naloxone. The naloxone was dissolved in saline.

The mice were given a charcoal meal (10 ml/kg of a 10% suspension) one hour after an oral dose of the vehicle or a test compound(s). Thirty minutes after the charcoal meal the mice were sacrificed by cervical dislocation and the distance in millimeters that the charcoal meal traveled through the small intestine was measured and compared to the controls.

6. Fecal Output Tolerance Study in Rats

Male Wistar rats (140–180 g) were given oral doses of either test compound, diphenoxylate HCl (suspended in methylcellulose or the vehicle (distilled water or methylcellulose) once a day for five consecutive days. Vehicle or the test compound were given daily 30 minutes before fecal collection. The feces were collected in a completely automated four-tiered metabolic cage over a 12-hour period consisting of three, four-hour intervals. Following collection, the feces were dried for four hours at 200° C. and weighed.

7. Prostaglandin test

An intraperitoneal injection of 100 micrograms per kilogram of $PGE_2$ causes diarrhea in mice within ten minutes. Groups of mice were orally dosed with test compound at various dose levels after which the $PGE_2$ is given and ten minutes later the mice are checked for diarrhea to determine the $ED_{50}$.

The amidinourea starting materials, in addition to having antidiarrheal properties, possess other pharmacological activities such as local anesthetic and cardiovascular activity. Unlike the amidinoureas which generally have local anesthetic properties, the pharmaceutically useful 1-heterocyclic alkylene-1,2-dihydro-1,3,5-triazin-2-ones and thiones of this invention are more specific and possess little or no classical local anesthetic effects, nor do they possess significant cardiovascular effects. The compounds of Formula I are particularly useful as antidiarrheal agents where it is desirable to achieve an antidiarrheal effect with a minimum of side effects and these compounds are therefore especially suited to the treatment of gastrogenic diarrhea.

The tests employed to determine the separation of local anesthetic and cardiovascular activity at effective antidiarrheal doses with representative compounds of the formula above are described below.

Several different procedures generally employed in testing for local anesthetic activity ar used to determine local anesthetic effects. These tests have been used extensively in the past and have given satisfactory results in defining the local anesthetic properties of compounds.

A discussion of experimental methods for evaluating local anesthetic properties of drugs is found in *Evaluation of Drug Activities: Pharmacometrics*, Vol. 1, Ed by D. R. Lawrence and A. L. Bacharach, Academic Press, Inc. (London) Ltd. (1964). Applicants herewith incorporate by reference Chapter 9 of this book entitled "Local Anesthetics", pages 204–214.

Tests which show the lack of side effects of the preferred amidinourea compounds include the following:

1. Effect of hexobarbital-Induced Loss of Righting Reflex

The test compound and a vehicle given orally thirty minutes before hexobarbital were compared for their effect on the duration of the loss of righting reflex (failure to right within five seconds) induced in groups of Swiss Webster mice (10/group, 18–20 g) by the intraperitoneal injection of hexobarbital (100 mg/kg, I.P.).

2. Effect of Plasma Glucose in Rats

Groups of 5–10 male Sprague-Dawley rats (170–210 g) were orally dosed with the test compound or the vehicle. Three hours after dosing, the rats were sacrificed by decapitation and blood was collected for plasma glucose evaluation.

3. Effect of Inducing Emesis in Dogs

Female beagle dogs (6–10 kg) were randomly selected for intravenous dosing with the test compound. Each dose of the test compounds was given to either two or four dogs. Immediately after the injection, the dogs were observed for emesis for a period of up to one hour.

Certain of the compounds possess differentiated levels of effectiveness as antisecretory or antimotility agents when administered in generally used tests in laboratory animals which tests are known to correlate to human application. The following test is utilized in establishing the antisecretory activity of the triazine derivatives.

Inhibition of Gastric Acid Secretion in the Rat

The method used has been reported by Shay. Male Sprague-Dawley rats (140–160 g) were fasted 24 hours prior to the test. The rats were allowed water ad libitum only during the fasting period. One hour before pyloric ligation, the rats (5/group) were given either the test compound, atropine sulfate or the vehicle. The compounds were prepared in methylcellulose. Pyloric ligation was performed in the rats under sodium methohexital anesthesia. Four hours after pyloric ligation the rats were sacrificed by cervical dislocation, the stomachs were removed, and the gastric contents were assayed for volume, titratable acidity, and titratable acid output (TAO). A 1 ml aliquot of the gastric contents was titrated with 0.1 N NaOH to pH 7.0 for titratable acidity. The percent of inhibition was calculated according to the formula:

$$\frac{\text{Mean control} - \text{mean treated}}{\text{Mean control}} \times 100$$

In general, compounds of Formula I are indicated for use as pharmacotherapeutic agent in a wide variety of mammalian conditions which require relief of symptoms or altering the action of the gastrointestinal or neuro-muscular systems. These compounds when used for example, as antidiarrheal, antisecretory or antispasmodic agents, are effective for these purposes when administered orally and/or parenterally. The term "parenteral" as used herein includes intravenous, intramuscular, intraperatoneal and the like injection or infusion techniques.

The dosage regimens in carrying out the pharmacotherapeutic methods utilizing the triazin-2-ones and triazin-2-thiones of this invention are those which insure maximum therapeutic response until improvement is obtained and thereafter the minimum effective level which gives relief. Thus, in general, the dosages are those that are therapeutically effective in the treatment of diarrhea and related gastrointestinal disorders. In general, the oral daily dose can be between about 0.1 mg/kg and 70 mg/kg (preferably in the range of 0.5–50 mg/kg/day), bearing in mind, of course, that in selecting the appropriate dosage in any specific case, consideration must be given to the patient's weight, general health, age, and other factors which may influence response to the drug.

Compositions intended for oral use may be prepared according to any method known to the art for the manufacture of pharmaceutical compositions and such compositions may contain one or more agents selected from the group consisting of sweetening agents, flavoring agents, coloring agents and preserving agents, in order to provide a pharmaceutically elegant and palatable preparation. Orally, they may be administered in tablets, aqueous or oily suspensions, dispersible powders or granules, emulsions, hard or soft capsules, or syrups or elixers. Tablets which contain the active ingredient in admixture with non-toxic pharmaceutically acceptable excipients are suitable for the manufacture of tablets. These excipients may be, for example, inert diluents, for example, calcium carbonate, sodium carbonate, lactose, calcium phosphate or sodium phosphate; granulating and disintegrating agents, for example, maize starch or alginic acid; binding agents, for example, starch, gelatin or acacia; and lubricating agents, for example, magnesium stearate, stearic acid or talc. The tablets may be uncoated or they may be coated by known techniques to delay disintegration and absorption.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with an oil medium, for example, arachis oil, liquid paraffin or olive oil.

Aqueous solutions containing the active substance and similar compositions formulated for ease of administration depending upon the particular therapeutic or prophylactic objective form a separate development with respect to the active compound disclosed herein. Excipients suitable for aqueous suspensions, may be employed if desired. These excipients are suspending agents, for example, sodium carboxymethyl-cellulose, methyl-cellulose, hydroxypropylmethylcellulose, sodium alginate, polyvinylpyrrolidine, gum tragacanth and gum acacia; dispersing or wetting agents may be a naturally occurring phosphatide, for example, lecithin; or condensation products of an alkylene oxide with fatty acids, for example, polyoxyethylene stearate; or condensation products of ethylene oxide with long-chain aliphatic alcohols, for example, heptadecaethyleneoxy-cetanol; or condensation products of ethylene oxide with partial esters derived from fatty acids and a hexitol, for example, polyoxyethylene sorbitol monooleate; or condensation products of ethylene oxide with partial esters derived from fatty acids and hexitol anhydrides, for example, polyoxyethylene sorbitan monoleate. The said aqueous suspensions may also contain one or more preservatives, for example, ethyl, or n-propyl, p-hydroxy benzoate, one or more coloring agents, one or more flavoring agents, and one or more sweetening agents, such as sucrose.

Oily suspensions may be formulated by suspending the active ingredient in a vegetable oil, for example, arachis oil, olive oil, sesame oil or coconut oil, or in a mineral oil, such as liquid paraffin. The oily suspensions may contain a thickening agent, for example, beeswax, hard paraffin or cetyl alcohol. Sweetening agents, such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending or wetting agents and suspending agents are exemplified by those already mentioned above. Additional excipients, for example, sweetening, flavoring and coloring agents, may also be present.

The compounds of this invention may also be in the form of oil-in-water emulsions. The oily phase may be a vegetable oil, for example, olive oil or arachis oils, or a mineral oil, for example, liquid paraffin or mixtures of these. Suitable emulsifying agents may be naturally-occurring gums, for example, gum acacia or gum tragacanth, naturally-occurring phosphatides, for example, soya bean lecithin, and esters or partial esters derived from fatty acids and hexitol anhydrides, for example, sorbitan mono-oleage. The emulsions may also contain sweeping and flavoring agents.

Syrups and elixirs may be formulated with sweetening agents, for example, glycerol, sorbitol or sucrose. Such formulations may also contain a demulcent, a preservative and flavoring and coloring agents. The pharmaceutical compositions may be in the form of a sterile injectionable preparation, for example, as a sterile injectable aqueous suspension. This suspension may be formulated according to the known art using those suitable dispersing or wetting agents and suspending agents which have been mentioned above. The sterile injectable preparation may also be a sterile injectable solution or suspension in a nontoxic parenterally-acceptable diluent or solvent, for example, as an aqueous solution buffered to a pH of 4.0 to 7.0 and made isotonic with sodium chloride.

Further, the active triazine may be administered alone or in admixture with other agents having the same or different pharmacological properties.

Further, these compounds may be tableted or otherwise formulated for oral use so that for every 100 parts by weight of the composition, there are present between 5 and 95 parts by weight of the active ingredient. The dosage unit form will generally contain between about 1 mg. and about 500 mg. of the active ingredients of this invention. The preferred unit dose is between about 10 mg. and about 100 mg. The compositions may be taken 1-8 times daily depending on the dosage unit required.

Parenteral administration may be carried out using comparative dosages taken from the oral compositions. In general, the parenteral dosage will be less than the oral dose and normally within the range of ½ to 1/10 the oral dose but, of course, this would depend on the absorption characteristics of the compound employed. Dosages would be in the customary manner; however, in general, parenteral administration may be carried out neat or the compound may be utilized with a sterile vehicle as mentioned above. Dosage unit forms between 1 mg. and 500 mg. and preferably in the range of 10 mg. and 100 mg. are useful. The daily parenteral dose would be between 0.1 mg/Kg/day and 70 mg/Kg/day and preferably in the range of 0.5 mg/Kg and 50 mg/Kg/day.

The compounds of this invention are also useful as veterinary medicines. In particular, these compounds are useful in the treatment of animal scours, particularly in food animals. When administered in suitable formulations, for example, as additives to food or water, these compounds prevent or relieve scours in lambs, calves, piglets and fowl.

We claim:

1. A compound of the formula

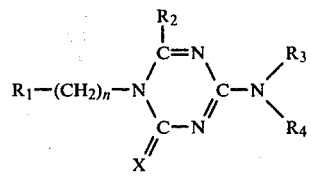

wherein:
n is 1 to 3;
X is oxygen or sulfur;
$R_1$ is a 5 or 6 membered heterocycle or a 5 or 6 membered heterocycle in which one or more of the hydrogens on the ring is replaced by the same or different substituents including halo, lower alkyl, halo lower alkyl, nitro, amino, acylamino, hydroxy, lower alkoxy, aryl-lower alkoxy, acyloxy, cyano, halo-lower alkoxy, or lower alkyl sulfonyl;
$R_2$ is hydrogen or lower alkyl; and
$R_3$ and $R_4$ are each independently selected from the group consisting of hydrogen, hydroxyl, lower alkanoyl, lower alkyl, cyclo-lower alkyl, lower alkenyl, lower alkynyl, halo-lower alkyl, lower alkoxy-lower alkyl, hydroxy-lower alkyl, phenoxy-lower alkyl, diloweralkyl amino, aryl or aryl-lower alkyl, lower alkoxy, phenoxy, a 5 or 6 membered heterocycle or a lower alkyl substituted 5 or 6 membered heterocycle or $R_3$ and $R_4$ together with the nitrogen to which they are attached form a 3 to 7 membered heterocyclic ring, selected from the group consisting of oxazolidinyl, thiazolidinyl, pyrazolidinyl, imidazolidinyl, piperidyl, azepinyl, piperazinyl, thiamorpholinyl, trimethylenetriaminyl, ethyleneiminyl, and morpholinyl;
and wherein:
aryl means phenyl or phenyl in which one or more of the phenyl hydrogens has been replaced by the same or different substituents selected from the group consisting of halo, lower alkyl, halo-lower alkyl, nitro, amino, lower alkyl acylamino, lower alkyl acyloxy, hydroxy, lower alkoxy, phenyl-lower alkoxy, lower alkanoyl, cyano, halo-lower alkoxy and lower alkyl sulfonyl; and
5 or 6 membered heterocycle means a heterocyclic substituent selected from the group consisting of pyridyl, pyrimidyl, pyrazolyl, imidazolyl, furyl, thienyl, oxazolyl, thiazolyl, piperidyl, and morpholinyl; and the nontoxic pharmaceutically acceptable salts thereof.

2. A compound of the formula

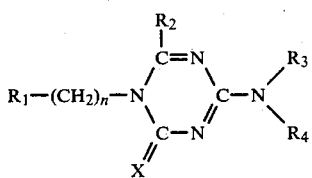

wherein X is oxygen or sulfur; $R_1$ is pyridyl, thiophenyl or furyl; or pyridyl, thiophenyl or furyl in which one or more of the ring hydrogens are substituted by lower alkyl, lower alkoxy, halo, halo-lower alkyl, amino, nitro, lower alkyl acyloxy, lower alkyl acylamino, hydroxy, cyano, carboxyl, or lower alkyl sulfonyl; $R_2$ is hydrogen or lower alkyl; and $R_3$ and $R_4$ are each independently selected from the group consisting of hydrogen, hydroxyl, lower alkanoyl, lower alkyl, lower alkenyl, lower alkynyl, lower alkoxy, halo-lower alkyl, hydroxy-lower alkyl, lower alkoxy-lower alkyl, phenoxy-lower alkyl, di-lower alkyl-amino-lower alkyl or $R_3$ and $R_4$ together with the nitrogen to which they are attached form a 5 or 6 membered nitrogen heterocycle selected form the group consisting of oxazolidinyl, thiazolidinyl, pyrazolidinyl, imidazolidinyl, piperidyl, piperazinyl, thiamorpholinyl, and morpholinyl; and the pharmaceutically acceptable nontoxic salts thereof.

3. A compound of the formula

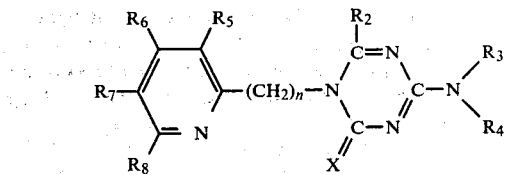

wherein:
n is 1 to 3;
$R_2$ is hydrogen or lower alkyl;
$R_3$ and $R_4$ are each independently selected from the group consisting of hydrogen, hydroxyl, lower alkanoyl, lower alkyl, cyclo-lower alkyl, lower alkenyl, lower alkynyl, halo-lower alkyl, lower alkoxy-lower alkyl, hydroxy-lower alkyl, phenoxy-lower alkyl, diloweralkylamino, aryl or aryl-lower alkyl, lower alkoxy, phenoxy and 5 or 6 membered heterocycles selected from the group consisting of pyridyl, pyrimidyl, pyrazolyl, imidazolyl, furyl, thienyl, oxazolyl, piperidyl and morpholinyl, or $R_3$ and $R_4$ together with the nitrogen to which they are attached form a 3 to 7 membered ring selected from the group consisting of oxazolidinyl, thiazolidinyl, pyrazolidinyl, imidazolidinyl, piperidyl, piperazinyl, thiamorpholinyl, trimethylenetriaminyl, ethyleneiminyl, and morpholinyl; and
$R_5$, $R_6$, $R_7$ and $R_8$ are each independently selected from the group consisting of hydrogen, lower alkyl, lower alkoxy, halo, halo-lower alkyl, amino, nitro, lower alkyl acyloxy, lower alkyl acylamino, hydroxy, cyano, carboxyl, or lower alkyl sulfonyl; and wherein:
aryl means phenyl or phenyl in which one or more of the phenyl hydrogens has been replaced by the same or different substituents selected from the group consisting of halo, lower alkyl, halo-lower alkyl, nitro, amino, lower alkyl acylamino, lower alkyl acyloxy, hydroxy, lower alkoxy, phenyl-lower alkoxy, lower alkanoyl, cyano, halo-lower alkoxy and lower alkyl sulfonyl; and the nontoxic pharmaceutically acceptable salts thereof.

4. A compound according to claim 1, 2 or 3 wherein X is oxygen.

5. A compound according to claim 3 wherein each of $R_6$, $R_7$ and $R_8$ is hydrogen; and the nontoxic pharmaceutically acceptable salts thereof.

6. A compound according to claim 1, 2, 3 or 5 wherein $R_3$ is hydrogen; and the nontoxic pharmaceutically acceptable salts thereof.

7. A compound according to claim 3 or 5 wherein $R_5$ is halo, lower alkyl, lower alkoxy, or halo-lower alkyl; and the nontoxic pharmaceutically acceptable salts thereof.

8. A compound of the formula

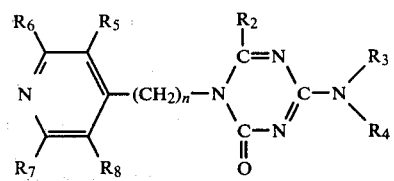

wherein:
n is 1 to 3;
$R_2$ is hydrogen or lower alkyl;
$R_3$ and $R_4$ are each independently selected from the group consisting of hydrogen, hydroxyl, lower alkanoyl, lower alkyl, cycloloweralkyl, lower alkenyl, lower alkynyl, halo-lower alkyl, lower alkoxy-lower alkyl, hydroxy lower alkyl, phenoxy lower alkyl, diloweralkylamino, aryl or aryl lower alkyl, lower alkoxy, and phenoxy, and 5 or 6 membered heterocycles selected from the group consisting of pyridyl, pyrimidyl, pyrazolyl, imidazolyl, furyl, thienyl, oxazolyl, thiazolyl, piperidyl, and morpholinyl, or $R_3$ and $R_4$ together with the nitrogen to which they are attached form a 3 to 7 membered ring selected from the group consisting of oxazolidinyl, thiazolidinyl, pyrazolidinyl, imidazolidinyl, piperidyl, piperazinyl, thiamorpholinyl, trimethylenetriaminyl, ethyleneiminyl, and morpholinyl;
$R_5$, $R_6$, $R_7$ and $R_8$ are each independently selected from the group consisting of hydrogen, lower alkyl, lower alkoxy, halo, halo-lower alkyl, amino, nitro, lower alkyl, acyloxy, lower alkyl acylamino, hydroxy, cyano, carboxyl, or lower alkyl sulfonyl;
and wherein:
aryl means phenyl or phenyl in which one or more of the phenyl hydrogens has been replaced by the same or different substituents selected from the group consisting of halo, lower alkyl, halo-lower alkyl, nitro, amino, lower alkyl acylamino, lower alkyl acyloxy, hydroxy, lower alkoxy, phenyl-lower alkoxy, lower alkanoyl, cyano, halo-lower alkoxy and lower alkyl sulfonyl; and the nontoxic pharmaceutically acceptable salts thereof.

9. A compound according to claim 8 wherein $R_3$ is hydrogen; and the nontoxic pharmaceutically acceptable salts thereof.

10. A compound according to claim 9 wherein $R_2$ is hydrogen and $R_4$ is hydrogen, lower alkyl, hydroxyl or lower alkoxy; and the nontoxic pharmaceutically acceptable salts thereof.

11. A compound according to claim 10 wherein $R_5$ and $R_8$ are each independently lower alkyl, lower alkoxy, halo, or halo-lower alkyl.

12. A compound of the formula

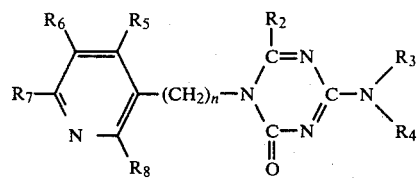

wherein:

n is 1 to 3;

$R_2$ is hydrogen or lower alkyl;

$R_3$ and $R_4$ are each independently selected from the group consisting of hydrogen, hydroxyl, lower alkanoyl, lower alkyl, cycloloweralkyl, lower alkenyl, lower alkynyl, halo-lower alkyl, lower alkoxy-lower alkyl, hydroxy lower alkyl, phenoxy lower alkyl, diloweralkylamino, aryl or aryl lower alkyl, lower alkoxy, and phenoxy, and 5 or 6 membered heterocycles selected from the group consisting of pyridyl, pyrimidyl, pyrazolyl, imidazolyl, furyl, thienyl, oxazolyl, thiazolyl, piperidyl, and morpholinyl, or $R_3$ and $R_4$ together with the nitrogen to which they are attached form a 3 to 7 membered ring selected from the group consisting of oxazolidinyl, thiazolidinyl, pyrazolidinyl, imidazolidinyl, piperidyl, piperazinyl, thiamorpholinyl, trimethylenetriaminyl, ethyleneiminyl, and morpholinyl;

$R_5$, $R_6$, $R_7$ and $R_8$ are each independently selected from the group consisting of hydrogen, lower alkyl, lower alkoxy, halo, halo-lower alkyl, amino, nitro, lower alkyl, acyloxy, lower alkyl acylamino, hydroxy, cyano, carboxyl, or lower alkyl sulfonyl; and wherein:

aryl means phenyl or phenyl in which one or more of the phenyl hydrogens has been replaced by the same or different substituents selected from the group consisting of halo, lower alkyl, halo-lower alkyl, nitro, amino, lower alkyl acylamino, lower alkyl acyloxy, hydroxy, lower alkoxy, phenyl-lower alkoxy, lower alkanoyl, cyano, halo-lower alkoxy and lower alkyl sulfonyl;

and the nontoxic pharmaceutically acceptable salts thereof.

13. A compound according to claim 12 wherein $R_3$ is hydrogen; and the nontoxic pharmaceutically acceptable salts thereof.

14. A compound according to claim 13 wherein $R_2$ is hydrogen and $R_4$ is hydrogen, lower alkyl, hydroxyl or lower alkoxy; and the nontoxic pharmaceutically acceptable salts thereof.

15. A compound according to claim 14 wherein $R_5$ and $R_8$ are each independently lower alkyl, lower alkoxy, halo, or halo-lower alkyl.

16. A compound of the formula

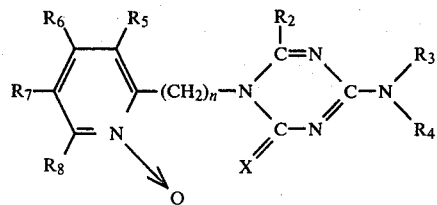

wherein:

n is 1 to 3;

$R_2$ is hydrogen or lower alkyl;

$R_3$ and $R_4$ are each independently selected from the group consisting of hydrogen, hydroxyl, lower alkanoyl, lower alkyl, cyclo-lower alkyl, lower alkenyl, lower alkynyl, halo-lower alkyl, lower alkoxy-lower alkyl, hydroxy-lower alkyl, phenoxy-lower alkyl, diloweralkylamino, aryl or aryl-lower alkyl, lower alkoxy, phenoxy and 5 or 6 membered heterocycles selected from the group consisting of pyridyl, pyrimidyl, pyrazolyl, imidazolyl, furyl, thienyl, oxazolyl, piperidyl and morpholinyl, or $R_3$ and $R_4$ together with the nitrogen to which they are attached form a 3 to 7 membered ring selected from the group consisting of oxazolidinyl, thiazolidinyl, pyrazolidinyl, imidazolidinyl, piperidyl, piperazinyl, thiamorpholinyl, trimethylenetriaminyl, ethyleneiminyl, and morpholinyl; and $R_5$, $R_6$, $R_7$ and $R_8$ are each independently selected from the group consisting of hydrogen, lower alkyl, lower alkoxy, halo, halo-lower alkyl, amino, nitro, lower alkyl acyloxy, lower alkyl acylamino, hydroxy, cyano, carboxyl, or lower alkyl sulfonyl; and wherein:

aryl means phenyl or phenyl in which one or more of the phenyl hydrogens has been replaced by the same or different substituents selected from the group consisting of halo, lower alkyl, halo-lower alkyl, nitro, amino, lower alkyl acylamino, lower alkyl acyloxy, hydroxy, lower alkoxy, phenyl-lower alkoxy, lower alkanoyl, cyano, halo-lower alkoxy and lower alkyl sulfonyl; and the nontoxic pharmaceutically acceptable salts thereof.

17. A compound according to claim 16 wherein $R_3$ is hydrogen; and the nontoxic pharmaceutically acceptable salts thereof.

18. A compound according to claim 15 wherein $R_5$ is halo, lower alkyl, lower alkoxy, or halo-lower alkyl; and the nontoxic pharmaceutically acceptable salts thereof.

19. 1-(2'-pyridylmethyl)-4-methylamino-1,2-dihydro-1,3,5-triazin-2-one; and the non-toxic pharmaceutically acceptable salts thereof.

20. 1-(2'-pyridylmethyl)-4-amino-1,2-dihydro-1,3,5-triazin-2-one; and the non-toxic pharmaceutically acceptable salts thereof.

21. A process for the preparation of a compound according to the Formula I:

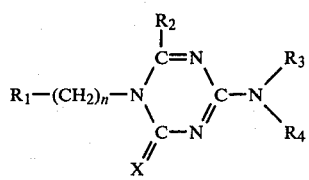

which comprises reacting under cyclization conditions an activated methylidene compound and an amidinourea compound of Formula II

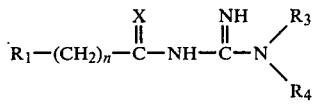

wherein:
n is 1 to 3;
X is oxygen or sulfur;
$R_1$ is a 5 or 6 membered heterocycle or a substituted 5 or 6 membered heterocycle;
$R_2$ is hydrogen or lower alkyl; and
$R_3$ and $R_4$ are each independently selected from the group consisting of hydrogen, hydroxyl, lower alkanoyl, lower alkyl, cyclo-lower alkyl, lower alkenyl, lower alkynyl, halo-lower alkyl, lower alkoxy-lower alkyl, hydroxy-lower alkyl, phenoxy-lower alkyl, diloweralkyl amino, aryl or aryl-lower alkyl, lower alkoxy, phenoxy, a 5 or 6 membered heterocycle or a lower alkyl substituted 5 or 6 membered heterocycle or $R_3$ and $R_4$ together with the nitrogen to which they are attached form a 3 to 7 membered heterocyclic ring, selected from the group consisting of oxazolidinyl, thiazolidinyl, pyrazolidinyl, imidazolidinyl, piperidyl, piperazinyl, thiamorpholinyl, trimethylenetriaminyl, ethyleneiminyl, and morpholinyl;
and wherein:
aryl means phenyl or phenyl in which one or more of the phenyl hydrogens has been replaced by the same or different substituents selected from the group consisting of halo, lower alkyl, halo-lower alkyl, nitro, amino, lower alkyl acylamino, lower alkyl acyloxy, hydroxy, lower alkoxy, phenyl-lower alkoxy, lower alkanoyl, cyano, halo-lower alkoxy and lower alkyl sulfonyl; and
5 or 6 membered heterocycle means a heterocyclic substituent selected from the group consisting of pyridyl, pyrimidyl, pyrazolyl, imidazolyl, furyl, thienyl, oxazolyl, thiazolyl, piperidyl, and morpholinyl;
and the nontoxic pharmaceutically acceptable salts thereof.

22. A process according to claim 21, wherein the activated methylidene compound is a dialkylacetal of a di-alkyl-lower carboxylic acid amide or the reaction product of a di-alkyl lower carboxylic acid amide and an alkylating agent.

23. A process according to claim 21, wherein the activated methylidene compound is a dialkylacetal of a di-alkyl-lower carboxylic acid amide in the presence of hydrogen ion.

* * * * *